(12) United States Patent
Mellert et al.

(10) Patent No.: US 10,870,891 B2
(45) Date of Patent: Dec. 22, 2020

(54) DIAGNOSTIC TEST SYSTEM FOR SPECIFIC, SENSITIVE AND REPRODUCIBLE DETECTION OF CIRCULATING NUCLEIC ACIDS IN WHOLE BLOOD

(71) Applicant: Biodesix, Inc., Boulder, CO (US)

(72) Inventors: Hestia Mellert, Boulder, CO (US); Leisa Jackson, Boulder, CO (US); Gary A. Pestano, Boulder, CO (US)

(73) Assignee: BIODESIX, INC., Boulder, CO (US)

( * ) Notice: Subject to any disclaimer, the term of this patent is extended or adjusted under 35 U.S.C. 154(b) by 37 days.

(21) Appl. No.: 15/862,896

(22) Filed: Jan. 5, 2018

(65) Prior Publication Data

US 2018/0202005 A1 Jul. 19, 2018

Related U.S. Application Data

(60) Provisional application No. 62/442,578, filed on Jan. 5, 2017.

(51) Int. Cl.
| | | |
|---|---|---|
| *C12Q 1/68* | (2018.01) | |
| *C12Q 1/6886* | (2018.01) | |
| *C12Q 1/6851* | (2018.01) | |
| *C12Q 1/6844* | (2018.01) | |

(52) U.S. Cl.
CPC ......... *C12Q 1/6886* (2013.01); *C12Q 1/6844* (2013.01); *C12Q 1/6851* (2013.01); *C12Q 2600/112* (2013.01); *C12Q 2600/118* (2013.01)

(58) Field of Classification Search
None
See application file for complete search history.

(56) References Cited

U.S. PATENT DOCUMENTS

2016/0186239 A1 6/2016 Sinha

FOREIGN PATENT DOCUMENTS

| CN | 1012282268 A | * | 7/2008 | .................. 435/91.2 |
|---|---|---|---|---|
| WO | WO 2016/020710 | | 2/1916 | |
| WO | WO 03/089899 | | 10/2003 | |
| WO | WO 2015/063121 | | 5/2015 | |

OTHER PUBLICATIONS

Maron et al. (J of Clin Invest, 2007, 117(10):3007-3019) (Year: 2007).*
Norton et al. (Clin Biochem, 2013, 46:1561-1565) (Year: 2013).*
Elshimali et al. (Int J Mol Sci, 2013, vol. 14, p. 18925-18958) (Year: 2013).*
Beaver et al., "Detection of cancer DNA in plasma of patients with early-stage breast cancer." Clin Cancer Res 2014, 20:2643-50.
Extended European Search Report and Opinion issued in European Application No. 18150429.1, dated Oct. 16, 2018.
Funaki, N. O., et al. "Perioperative quantitative analysis of cytokeratin 20 mRNA in peripheral venous blood of patients with colorectal adenocarcinoma." *Oncology reports* 7.2 (2000): 271-277.
Hindson, Benjamin J., et al. "High-throughput droplet digital PCR system for absolute quantitation of DNA copy number." *Analytical chemists* 83.22 (2011): 8604-8610.
Oxnard, Geoffrey R., et al. "Noninvasive detection of response and resistance in EGFR-mutant lung cancer using quantitative next-generation genotyping of cell-free plasma DNA." *Clinical cancer research* (2014).
Partial European Search Report issued in European Application No. 18150429.1, dated Jul. 5, 2018.
Sacher, Adrian G., et al. "Prospective validation of rapid plasma genotyping for the detection of EGFR and KRAS mutations in advanced lung cancer." *JAMA oncology* 2.8 (2016): 1014-1022.
Soeth, Edlyn, et al. "The detection of disseminated tumor cells in bone marrow from colorectal-cancer patients by a cytokeratin-20-specific nested reverse-transcriptase-polymerase-chain reaction is related to the stage of disease." *International Journal of Cancer* 69.4 (1996): 278-282.
Takeshita, Takashi, et al. "Prognostic role of PIK 3 CA mutations of cell-free DNA in early-stage triple negative breast cancer." *Cancer science* 106.11 (2015): 1582-1589.
Weber, Britta, et al. "Detection of EGFR mutations in plasma and biopsies from non-small cell lung cancer patients by allele-specific PCR assays." *BMC cancer* 14.1 (2014): 294.
Office Communication issued in European Application No. 18150429.1, dated Dec. 19, 2019.

* cited by examiner

*Primary Examiner* — Stephanie K Mummert

(74) *Attorney, Agent, or Firm* — Parker Highlander PLLC

(57) ABSTRACT

The present disclosure relates to a rapid diagnostic test system that includes the prospective collection of whole blood, preservation of circulating nucleic acids at ambient temperature, and the reproducible detection of nucleic acids including DNA and mRNA (including fusion transcripts and differentially expressed transcripts) by different genomic methodologies.

15 Claims, 31 Drawing Sheets
(30 of 31 Drawing Sheet(s) Filed in Color)
Specification includes a Sequence Listing.

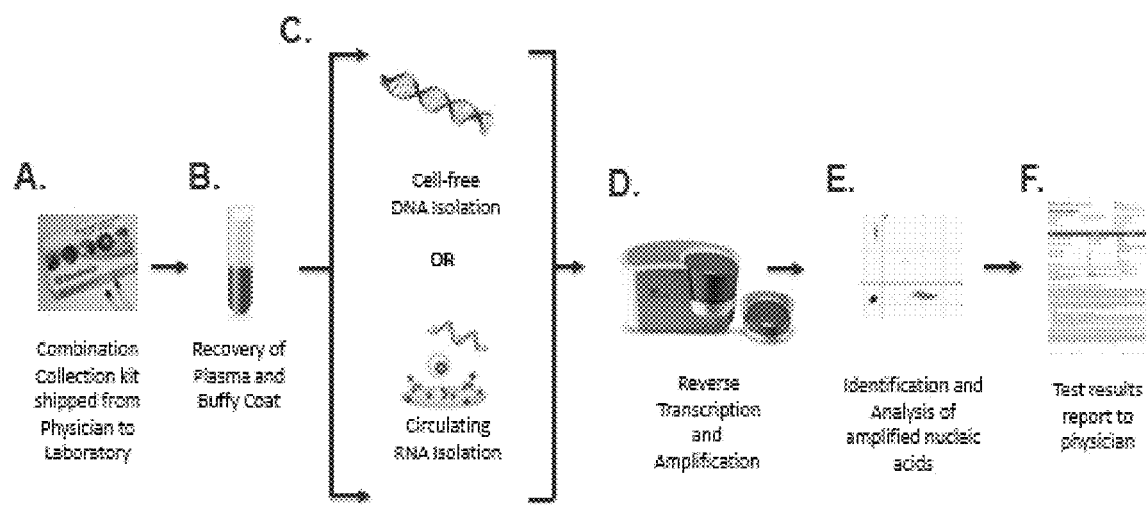
FIGS. 1A-F
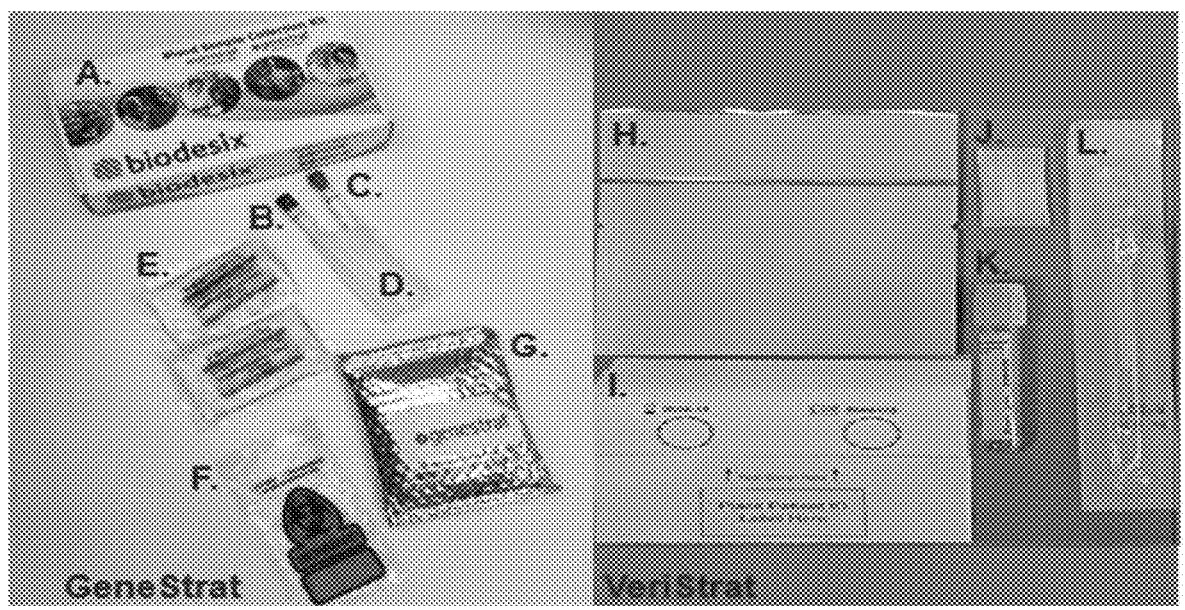
FIGS. 2A-L

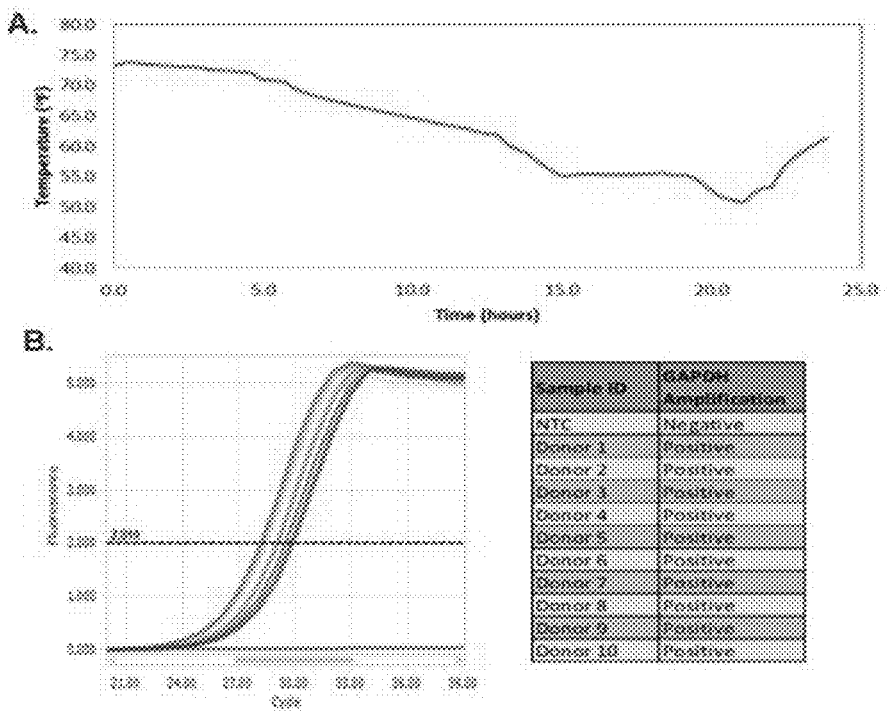
FIGS. 3A-B
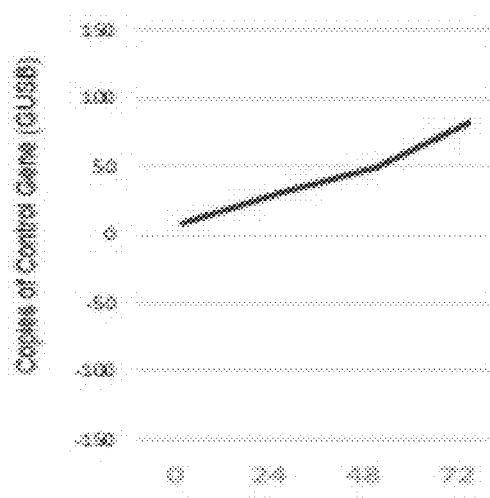
FIG. 4

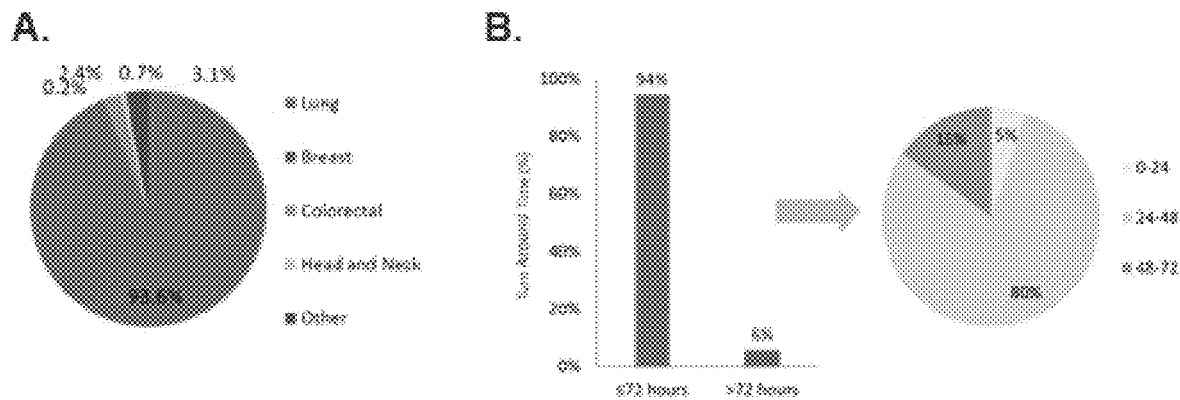
FIGS. 5A-C
FIGS. 6A-B

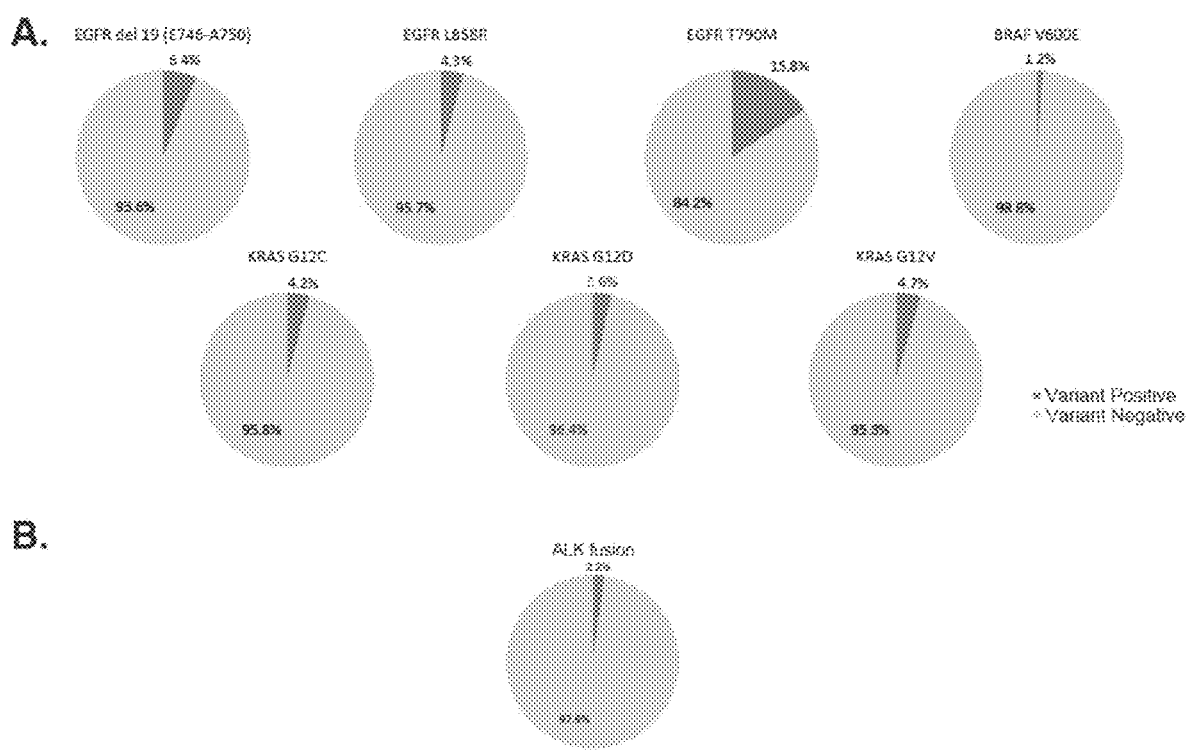
FIGS. 7A-B

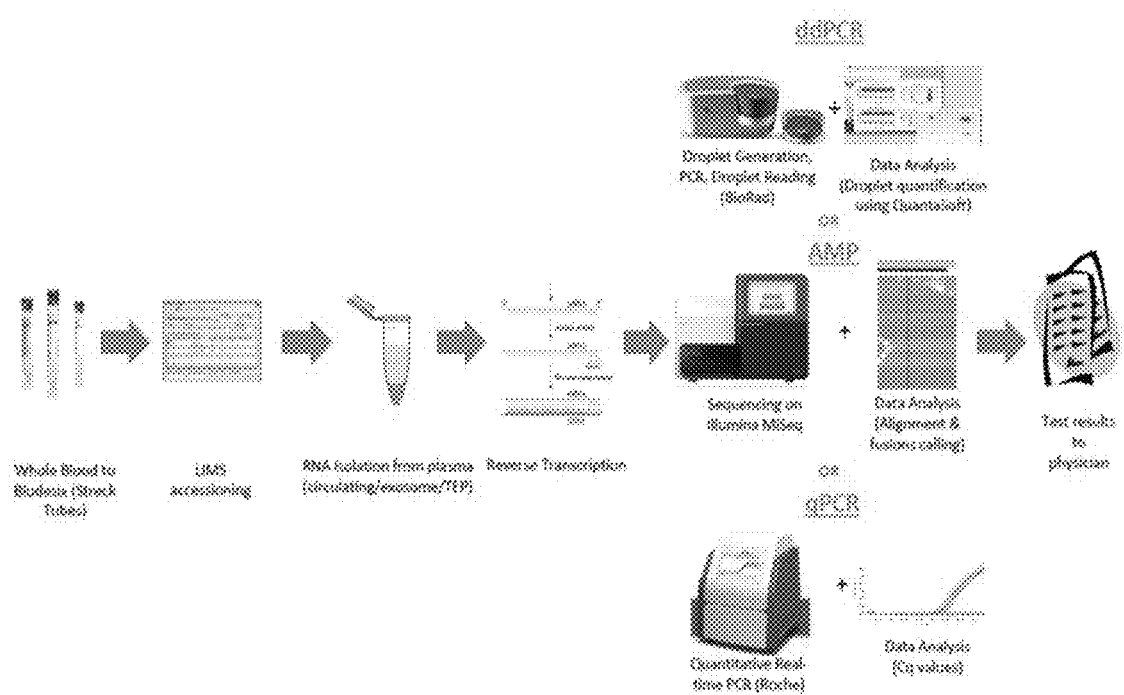
FIGS. 9A-B
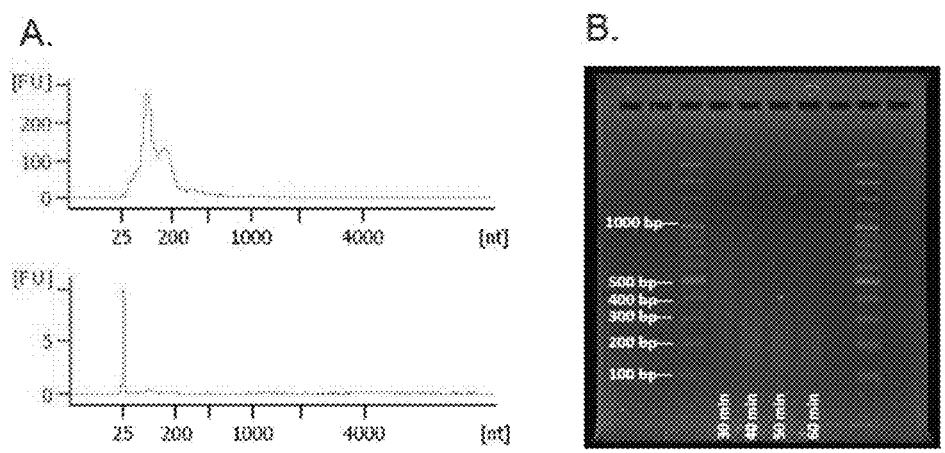
FIGS. 10A-B

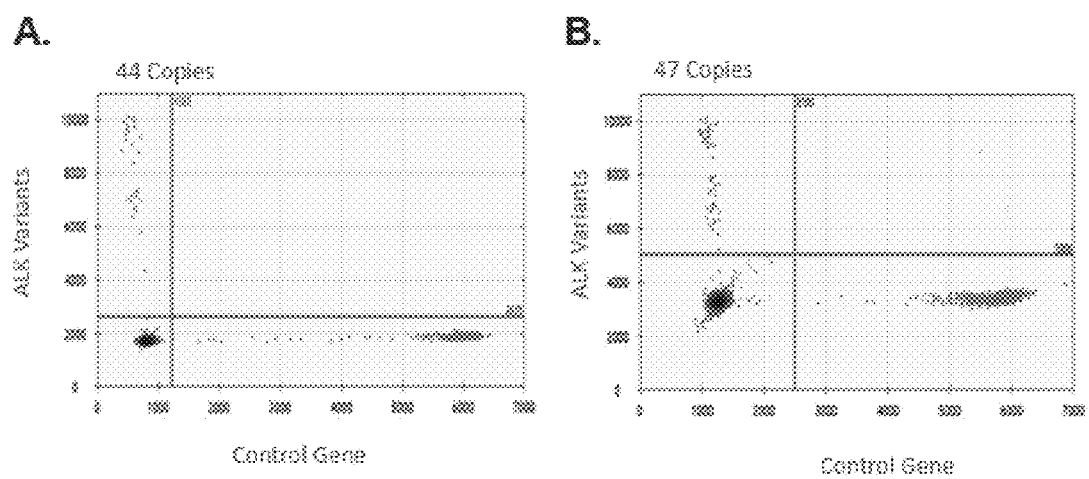
FIGS. 11A-F
FIGS. 12A-B

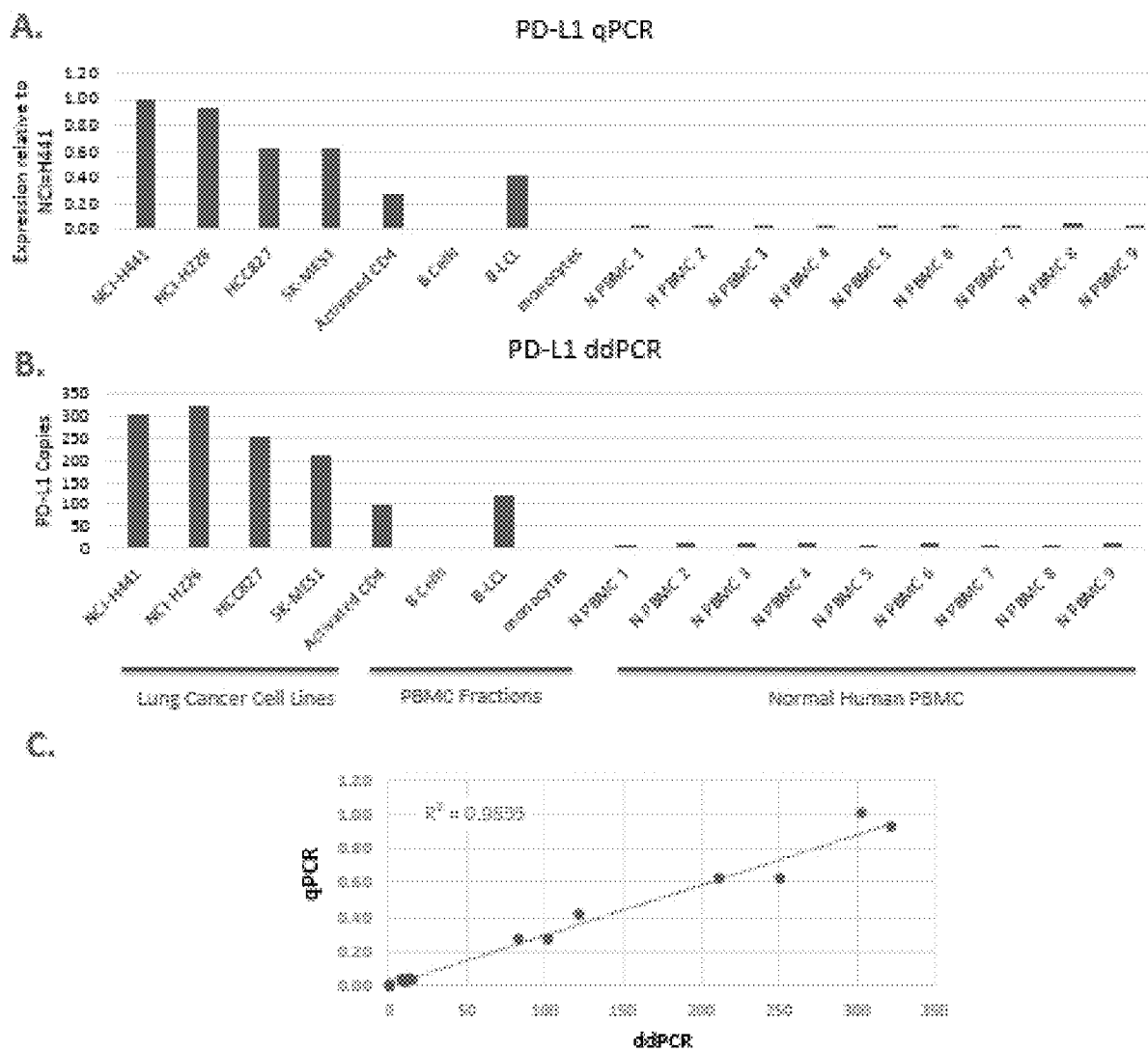
FIGS. 15A-C

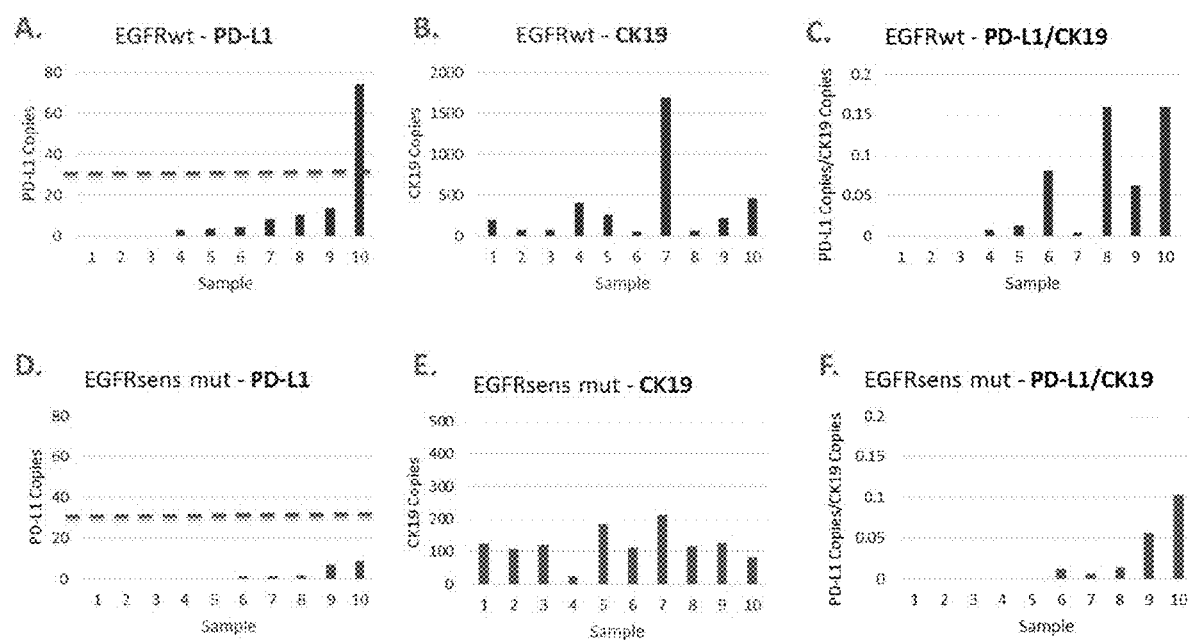
FIGS. 16A-D

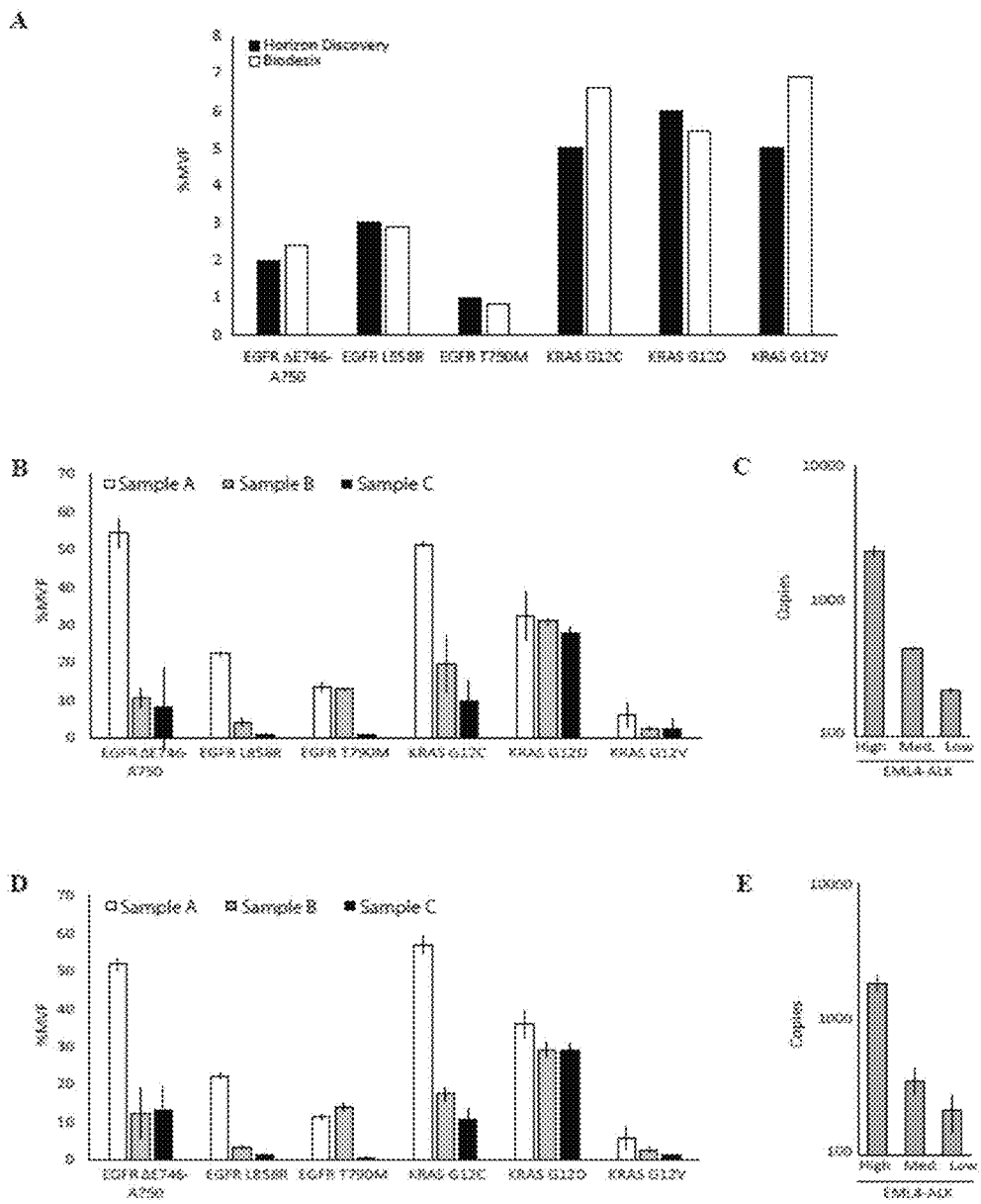
FIGS. 17A-E

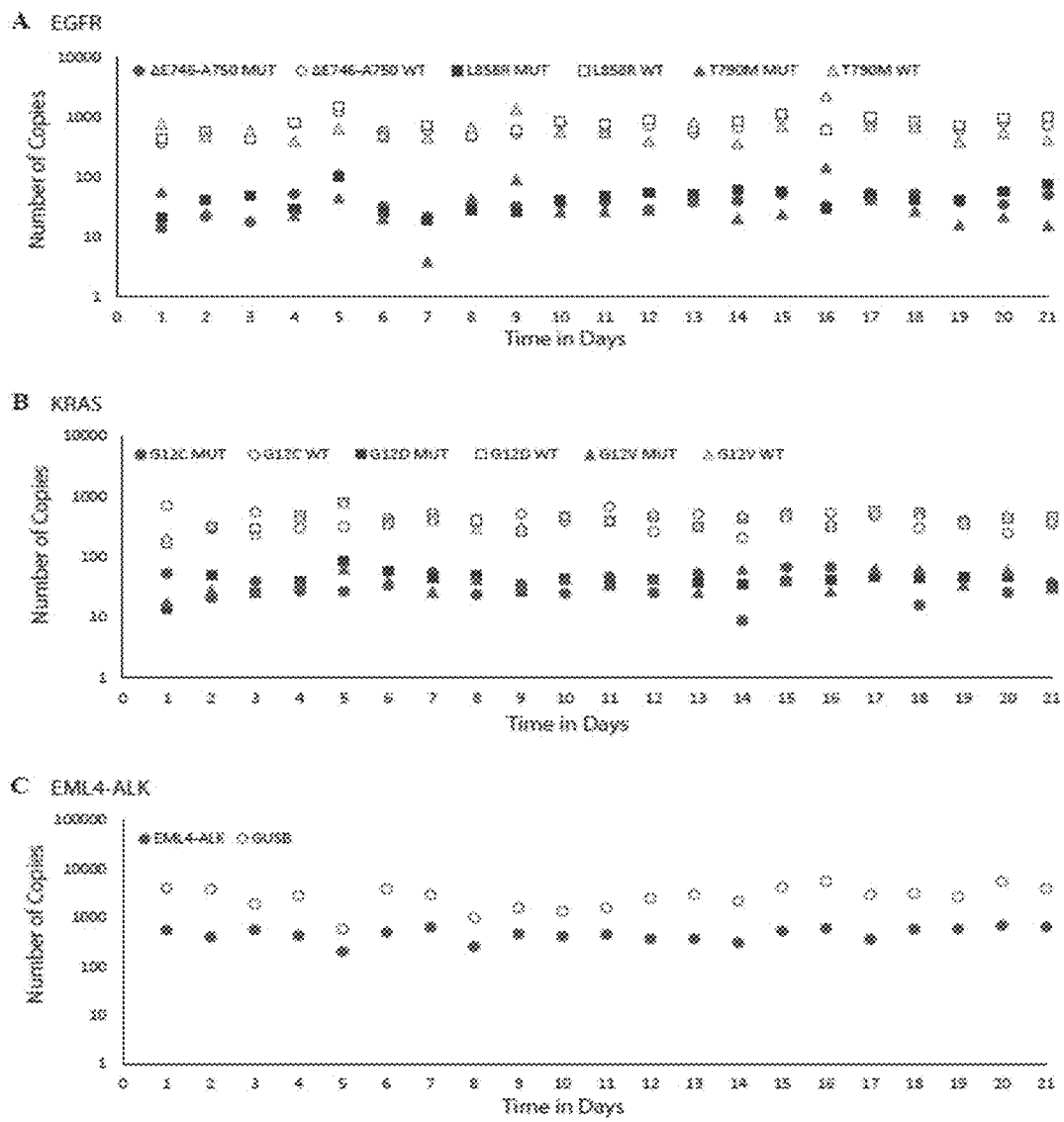
FIGS. 18A-C

FIGS. 19A-B

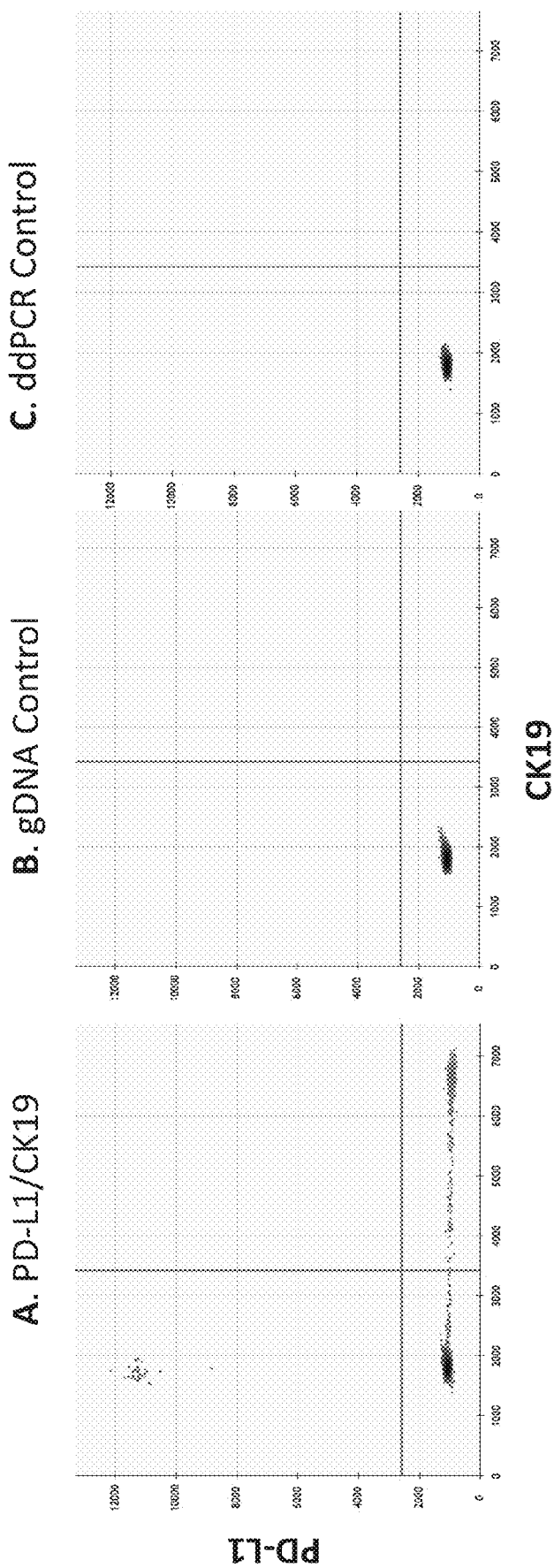
FIGS. 20A-C

SEQUENCE LISTING

<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: Synthetic probe

<400> SEQUENCE: 1
acgaccatcc aggacctgcg                                        20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

```
<400> SEQUENCE: 2
gcgactacag ccactactac                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gtggcaccaa gaatttgtcc                                              20
```

DIAGNOSTIC TEST SYSTEM FOR SPECIFIC, SENSITIVE AND REPRODUCIBLE DETECTION OF CIRCULATING NUCLEIC ACIDS IN WHOLE BLOOD

PRIORITY CLAIM

This application claims benefit of priority to U.S. Provisional Application Ser. No. 62/442,578, filed Jan. 5, 2017, the entire contents of which are hereby incorporated by reference.

BACKGROUND

I. Field

The present disclosure relates to the fields of molecular biology, diagnostics and medicine. More particularly, the disclosure relates to a rapid diagnostic test system that includes the prospective collection of whole blood, preservation of circulating nucleic acids at ambient temperature, and the reproducible detection of nucleic acids including DNA and mRNA (including fusion transcripts and differentially expressed transcripts) by different genomic methodologies.

II. Related Art

Approximately 30% of patients with advanced non-small cell lung cancer (NSCLC) are not candidates for tissue biopsies and in some cases where tissue is obtained, it is not always of sufficient quantity for molecular testing. Additionally, tissue-based genomic tests that rely on tissue do not easily resolve tumor heterogeneity at the systemic level and thus do not reflect both the primary and metastatic sites in an individual. Tissue diagnosis is primarily conducted on specific regions of an affected organ that have been biopsied. Thus sampling bias is inherent to tissue diagnosis in cancer. Moreover, genomic test results that rely on tissue disaggregation (e.g., PCR) are often contaminated by measures of nucleic acids in adjacent normal, or cancerous, non-rearranged tumor regions. Further complicating tissue testing for nucleic acids are the varied fixatives, time to fixation and time of fixation, all of which contribute to degradation and/or crosslinking of nucleic acids and subsequently overall poor performance and technical reproducibility of genomic tests being performed on tissue samples. For these reasons, testing for the detection of nucleic acids and other moieties in circulation has become increasingly relevant to clinical laboratory testing.

SUMMARY

The disclosure describes a blood-based diagnostic test system designed as a test service for the detection of clinically actionable variants in circulating nucleic acids isolated from whole blood samples from patients with cancer. Variant results may be reported within 72 hours of sample receipt at the laboratory. As described, exemplary components of the test system include: (a) defined kit and kit components to stabilize obtained blood samples, (b) specialized blood collection tubes, (c) prioritized shipment and sample receipt procedures, (d) assay optimization for reproducible nucleic acid recovery from plasma, including fresh and frozen platelet enriched plasma (PEP), (e) a digital PCR (dPCR) system optimized for rare event detection including those from somatic DNA variants, overexpressed mRNA and RNA from gene fusions, and (f) an electronic test result reporting that incorporates physician, patient, reimbursement, and treatment impact information as well as ddPCR-generated molecular test results.

More specifically, there is provided a method of detecting a fragmented nucleic acid in a freshly-collected whole blood sample from a mammalian subject comprising (a) recovering blood components from a whole blood sample from a mammalian subject, said blood components including plasma and buffy coat from the whole blood sample; (b) isolating free nucleic acid, nucleic acid associated with, exosomes and/or platelets in platelet enriched plasma (PEP), nucleic acid associated with PBMCs, or a combination thereof from said blood components; (c) purifying and concentrating the isolated nucleic acid of step (b); (d) amplifying said isolated nucleic acid of step (c) or a complimentary DNA generated from said nucleic acid of step (c); and (e) identifying and/or quantifying amplified nucleic acid from step (d). The method may further comprise obtaining a blood sample from the subject. Steps (a)-(e) may be performed in less than three days, even including the blood sampling. The mammalian subject may be a human.

The DNA may have sizes ranging between 100 and 300 nucleotides, and the RNA may have sizes ranging between 50 and 250 nucleotides. Step (b) may comprise isolating said nucleic acid from a whole blood sample that has been collected from mammalian donors into formaldehyde or formaldehyde-free preservatives and/or inhibitors of enzymes known to degrade nucleic acids. The method may further comprise reverse transcription of said RNA into complimentary DNA by a reverse transcriptase enzyme, such as SuperScript RT IV. The RNA may be an mRNA, such as an mRNA fusion, such as those that contain the 3' gene of either ALK, ROS1 and RET; or may comprise an mRNA differentially expressed for which said expression is known to affect cancer progression, such as PD-L1, PD1, CTLA4, keratins and other modulators of the immune system known to affect cancer progression.

Step (d) may comprise qPCR, ddPCR, RT-ddPCR in one or multiple steps, or AMP-PCR (Anchored Multiplex PCR) in single or multiplex format. Amplified nucleic acid or complimentary DNA generated in step (d) may be purified and concentrated, thereby maximizing quantity of said nucleic acid entered into amplification and decreasing non-specific signal, such as by size-exclusion columns. Step (b) may comprise isolating free nucleic acid and/or nucleic acid associated with exosomes and/or platelets in said PEP. Conversion of RNA to cDNA may comprise the use of single or multiplexed gene specific primers (GSPs). Step (d) may comprise nucleic acid sequencing, variant specific PCR, RT-PCR, qPCR and AMP-PCR. In some cases, 2 or more copies of variant target may be detected by ddPCR and maybe validated against mammalian donor samples as the cut-off for a positive DNA or RNA-fusion mutation. In other cases, 30 or more copies of differentially-expressed target may be detected by ddPCR and may be validated against mammalian donor samples as the cut-off for a positive result.

The method may further comprising generating an integrated test result report (iTRR) integrating physician information, patient information, reimbursement information, and/or treatment recommendation or impact, with the results from step (e), such as a VeriStrat® serum protein test result. The method may further comprise one or more control reactions. The method may comprise quantifying amplified nucleic acid from step (d) using ddPCR, qPCR, or NGS. The subject may be suspected of having cancer or has been diagnosed as having cancer. The nucleic acid may be obtained from components of the buffy-coat fraction of processed whole-blood from cancer patients, including but not limited to malignant tumor cells, lymphocytes, granulocytes, neutrophils, dendritic cells, such as wherein blood sample is obtained with a specimen collection kit configured for collection and ambient temperature shipment of fractionated or whole blood, wherein the collection kit is configured to allow downstream molecular proteomic and/or genomic analysis of the blood components.

In another embodiment, there is provided a method of predicting outcomes for a subject having been diagnosed with non-small cell lung cancer comprising (a) recovering blood components from a whole blood sample from said subject, said blood components including plasma and buffy coat from the whole blood sample; (b) isolating free nucleic acid, nucleic acid associated with, exosomes and/or platelets in platelet enriched plasma (PEP), nucleic acid associated with PBMCs, or a combination thereof from said blood components; (c) purifying and concentrating the isolated nucleic acid of step (b); (d) generating a cytokeratin complimentary DNA generated from said nucleic acid of step (c), amplifying a cytokeratin PCR product; (e) detecting cytokeratin nucleic acid, wherein a greater than average cytokeratin copy number in said sample indicates a worse than average prognosis for said subject. Step (d) may comprise ddPCR. The greater than average cytokeratin copy number may be 7 or more. The worse than average prognosis may comprise one or more of metastasis, reduced survival time, or reduced remission time. Step (e) may comprise detection of cytokeratin nucleic acid using a probe that hybridizes to an amplification product of step (d). The probe may be located across the junction of exons 1 and 2 of CK19, such as ACGACCATCCAGGACCTGCG (SEQ ID NO: 1), and may be labeled, such as with a fluorophore and/or quencher. Amplification of CK19 nucleic acid may comprise use of forward and reverse primers GCGACTACAGCCACTACTAC (SEQ ID NO: 2) and GTGGCACCAAGAATTTGTCC (SEQ ID NO: 3), respectively.

In still another embodiment, there is provided a method of detecting a cytokeratin nucleic acid in a sample comprising (a) obtaining a cytokeratin nucleic acid containing sample; (b) annealing forward and reverse primers that hybridize to said cytokeratin nucleic acid with said sample; (c) amplifying said cytokeratin nucleic acid; and (d) detecting cytokeratin nucleic acid. Step (c) may comprise ddPCR. Step (d) may comprise detection of cytokeratin nucleic acid using a probe that hybridizes to an amplification product of step (c). The probe may be located across the junction of exons 1 and 2 of CK19, such as ACGACCATCCAGGACCTGCG (SEQ ID NO: 1), and the probe may labeled, such as with a fluorophore and/or quencher. The forward and reverse primers may be GCGACTACAGCCACTACTAC (SEQ ID NO: 2) and GTGGCACCAAGAATTTGTCC (SEQ ID NO: 3), respectively. The cytokeratin nucleic acid may be an mRNA, a cDNA or cfDNA. The method may further comprise purifying and concentrating the cytokeratin nucleic acid prior to step (c). The sample may be whole blood.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, for the method being employed to determine the value, or that exists among the study subjects. Such an inherent variation may be a variation of ±10% of the stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIGS. 1A-F. Biodesix Workflow for The Lung Reflex Test. (FIG. 1A) The test process for GeneStrat® DNA test system and VeriStrat® protein test system is initiated when whole blood drawn into blood collection tubes (BCT) or serum spotted onto a dried blood spot card, arrives at the Laboratory. (FIG. 1B) In GeneStrat® testing, whole-blood is processed to isolate specific fractions including free nucleic acid; nucleic acid associated with, exosomes and/or platelets in platelet enriched plasma (PEP), PBMCs, or a combination of the aforementioned. (FIG. 1C) Nucleic acid is isolated and further processed. (FIG. 1D) In the case where RNA is the molecular target, reverse transcription is used to generate cDNA that is further processed. cDNA or cfDNA are amplified using a PCR-based method such as ddPCR. (FIG. 1E) Amplified nucleic acids can be identified and analysis is performed to call the target variants relative to an internal control. (FIG. 1F) An electronic individualized patient specific Test Result Reports (TRR) that integrates physician, patient, reimbursement, treatment impact, the VeriStrat® protein signature and the molecular test result is delivered back to the physician.

FIGS. 2A-L Specimen Collection Kit. The specimen collecting kit is designed for draw, processing and stable shipment of samples at ambient temperature for both the GeneStrat® and VeriStrat® tests in combination. The kit components are shipped in (FIG. 2A) the specimen collection combination kit box. This box contains components for use with the GeneStrat® test including (FIG. 2B) 10 ml Streck DNA BCT, (FIG. 2C) 10 ml Streck RNA BCT, (FIG. 2D) absorbent collection tube sleeve, (FIG. 2E) ambient temperature gel packs, (FIG. 2F) biohazard bag, (FIG. 2G) foil protective pouch. The box also contains components for use with the VeriStrat® test including (FIG. 2H) multi-barrier sample shipping pouch, (FIG. 2I) dried blood spot card, (FIG. 2J) desiccant pouch, (FIG. 2K) Greiner or BD serum separation tube, and (FIG. 2L) disposable transfer pipette.

FIGS. 3A-B. In-transit Ship Stability of the Specimen Collection Kit. (FIG. 3A) Blood collection tubes (n=10 individual donors with two each replicates) filled with whole blood from normal donors were drawn and shipped priority overnight to the Biodesix Laboratory with a temperature monitor. Temperatures were stabilized and with a variance of less than 25° F. Actual temperatures recorded ranged from a low of 50.8° F. to a high of 73.8° F. (FIG. 3B) Samples shipped at ambient temperature were received and processed using GeneStrat® procedures to recover circulating free DNA from 10 normal, healthy donors. DNA was processed using the GS plasma and cfDNA recovery protocols and detected with qPCR (Roche LightCycler). Samples were stable and recovered DNA was of sufficient quality for all samples to yield positive results for the test gene, GAPDH.

FIG. 4. RNA Stability within the Specimen Collection Kit over a 72 hour time period. A single donor supplied four whole blood samples of 10 ml each drawn into RNA BCT tubes (Streck) and packaged within the specimen collection kit. Samples were stored at ambient temperature until processing. One tube was processed immediately (t=0) and the remainder were processed at t=24, 48 and 72 hours. Expression of the control gene GUSB was evaluated by ddPCR at each time-point.

FIGS. 5A-C. Examples of GeneStrat® Test Performance. (FIG. 5A) Clinical validation study using 92 donor samples showing concordance of the GeneStrat® DNA test system relative to a reference standard (example shown is for EGFR delE746-A750). (FIG. 5B) Clinical validation study using 24 donor samples showing concordance of the GeneStrat® RNA test system relative to a reference standard (example shown is for EML4-ALK). (FIG. 5C) Clinical Sensitivity, Specificity and Concordance of the GeneStrat® test system relative to reference standards.

FIGS. 6A-B. Real World Examples of the GeneStrat® Test Workflow Performance. 1093 patient samples were evaluated over a three month period. (FIG. 6A) The GeneStrat® Test was performed in multiple cancer types including Lung, Breast, Colorectal, Head and Neck, and others. (FIG. 6B) 94% of total test result reports were delivered within 72 hour of receipt of the sample. Further, turnaround time of the majority of tests was within 48 hours. Data excludes weekends/holidays and samples held due to incomplete clinical data from physician entered into the Test Request Form.

FIGS. 7A-B. Representative GeneStrat® Variant Test Frequencies in the United States in 2016. The percentage of GeneStrat® variant tests that yielded either a Positive or a Negative result. (FIG. 7A) GeneStrat® DNA variants (n=1093 donor samples) and (FIG. 7B) GeneStrat® mRNA EML4-ALK fusion variants (n=272 donor samples).

(FIG. 8A) EGFR delE746-A750 mutation and EGFR wild-type control, (FIG. 8B) EGFR exon 19 deletion multiplex covering 15 variants and EGFR wild-type control, (FIG. 8C) EGFR L858R mutation and EGFR wild-type control, (FIG. 8D) EGFR T790M mutation and EGFR wild-type control, (FIG. 8E) KRAS G12C mutation and KRAS wild-type control, (FIG. 8F) KRAS G12D mutation and KRAS wild-type control, (FIG. 8G) KRAS G12V mutation and KRAS wild-type control, (FIG. 8H) KRAS multiplex covering seven mutations at amino acids 12 and 13 and KRAS wild-type control, (FIG. 8I) BRAF V600E mutation and BRAF wild-type control, (FIG. 8J) ALK fusion transcript multiplex assay covering 3 variants and control gene K. ALK fusion transcript multiplex assay covering three variants and a control gene (FIG. 8K) ROS1 fusion transcript multiplex assay covering eight variants and control gene (FIG. 8L) RET fusion transcript multiplex assay covering eight variants and control gene, (FIG. 8M) PD-L1 expression assay and control gene. CfDNA from clinical validation samples were used for FIGS. 8A-I, PEP-associated RNA was used in FIG. 8J and FIG. 8M, and RNA isolated from cell-lines is shown for FIG. 8K and FIG. 8L.

FIG. 9A-B. Alternative methods evaluated for the analysis of RNA fusions from blood. Methods shown include (FIG. 9A) AMP, NGS and (FIG. 9B) ddPCR.

FIGS. 10A-B. Nucleic Acid Preparation for ddPCR by the GeneStrat® test. (FIG. 10A) The fragmentation of RNA isolated from PEP according to the GeneStrat® test system procedures was evaluated using a BioAnalyzer. The RNA ranged between 50 and 250 nucleotides (top panel). A no RNA control well was run on the BioAnalyzer for comparison (bottom panel). RNA like that shown is readily converted to cDNA and amplified using the GeneStrat® RNA test workflow. (FIG. 10B) Genomic DNA fragmented by sonication and resolved on a 2% agarose gel. 100-300 bp fragments shown are readily amplified using the GeneStrat® DNA test workflow.

FIGS. 11A-F. Evaluation of Multiple Methods and Source Materials for Isolation of Circulating RNA from Whole Blood using qPCR or ddPCR. Six extraction methods (FIGS. A-D) and three source materials from whole blood (FIGS. D-F) were evaluated for circulating RNA yield. (FIGS. A-C) Yield was assessed using the qRT-PCR-based Archer PreSeq RNA QC Assay Protocol (ArcherDx) and results are reported as Ct values. (FIGS. D-F) Yield was assessed using the ddPCR for wild-type KRAS RNA (Bio-Rad) and ddPCR results are reported as absolute copy numbers. (FIGS. A-C). PEP: Platelet Enriched Plasma; PDP: Platelet Depleted Plasma; TEPs: Tumor Educated Platelets FIGS. 12A-B. Comparison of One-Step RT-ddPCR to Two-Step RT-ddPCR. EML4-ALK RNA fragments spiked into PEP and isolated using the GeneStrat® test system were used to evaluate RT-ddPCR. (FIG. 12A) Two-step process where cDNA synthesis reaction occurs before amplification. (FIG. 12B) One-step cDNA synthesis and amplification (single tube reaction).

(FIG. 13A) Purified cDNA was evaluated compared to unpurified cDNA. The circle surrounds positive droplets at high amplitude following purification. (FIG. 13B) Agencourt AMPure XP cleanup was compared to DNA Clean and Concentrator-5 (Zymo) using the sample. The Zymo purification method outperformed all methods.

Figure 8A:
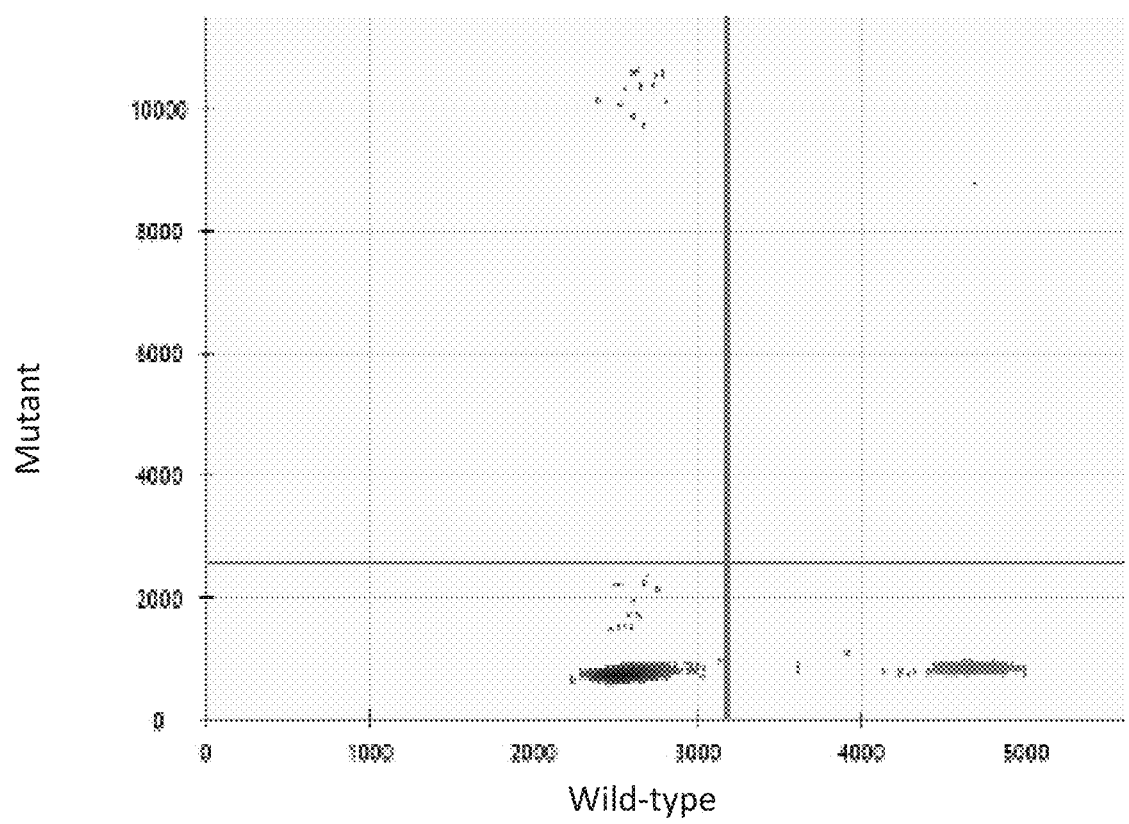
FIGS. 8A-M. Example of droplet distributions for positive samples using the GeneStrat® test system.
Figure 8B:
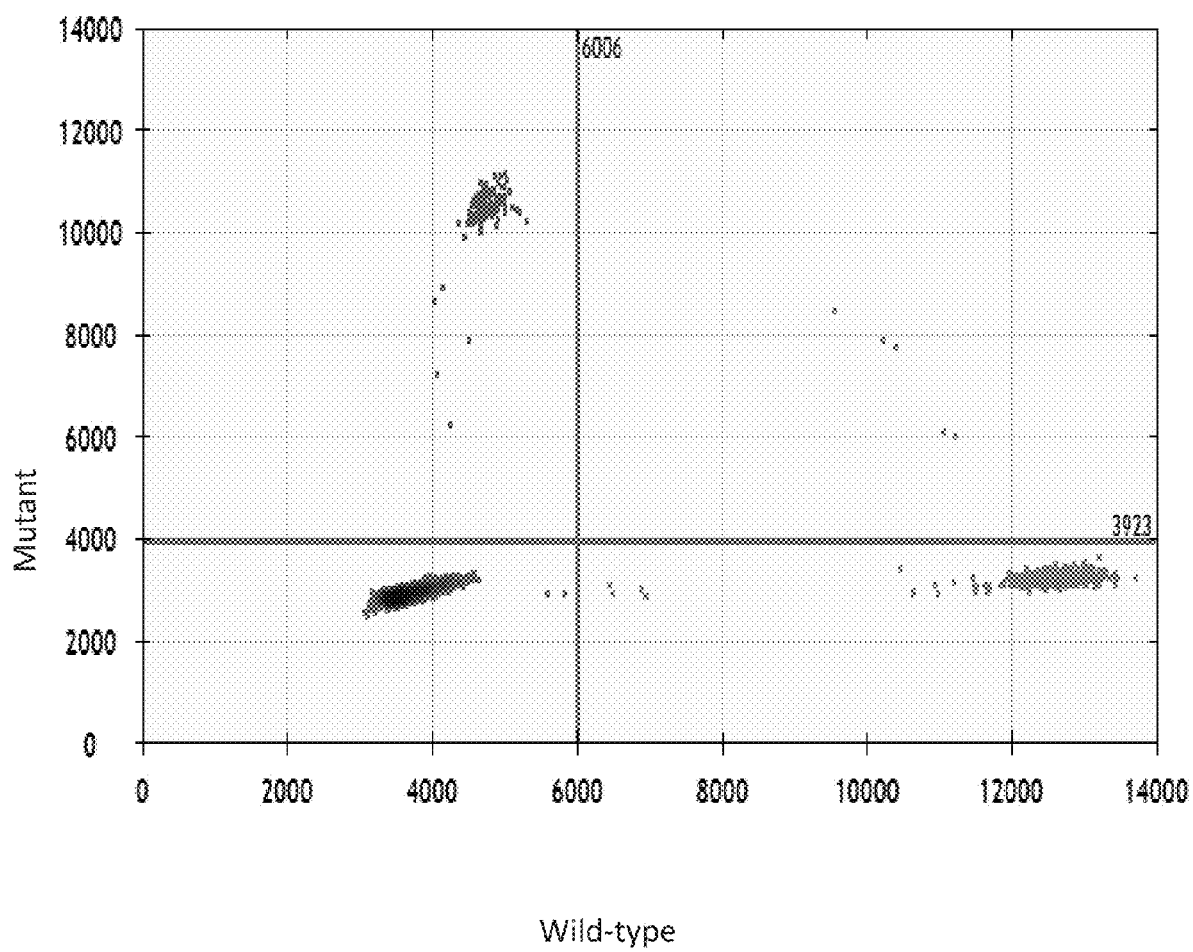
Figure 8C:
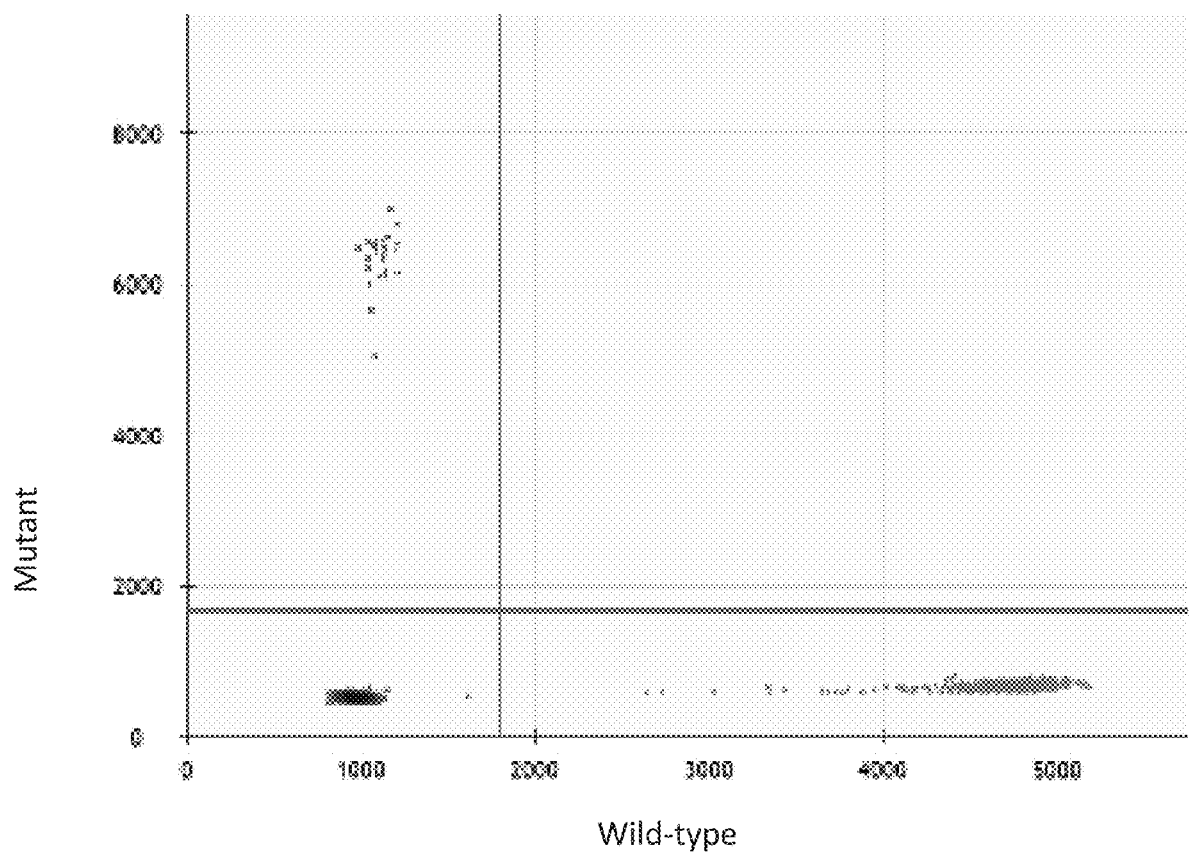
Figure 8D:
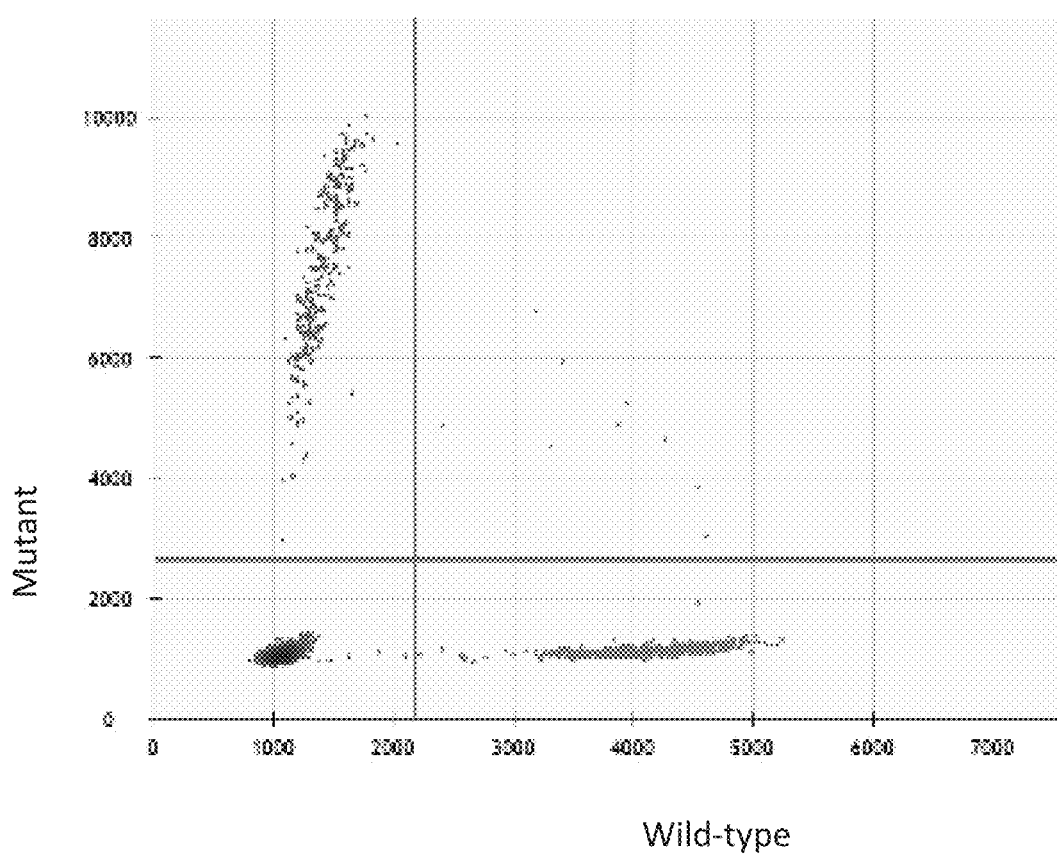
Figure 8E:
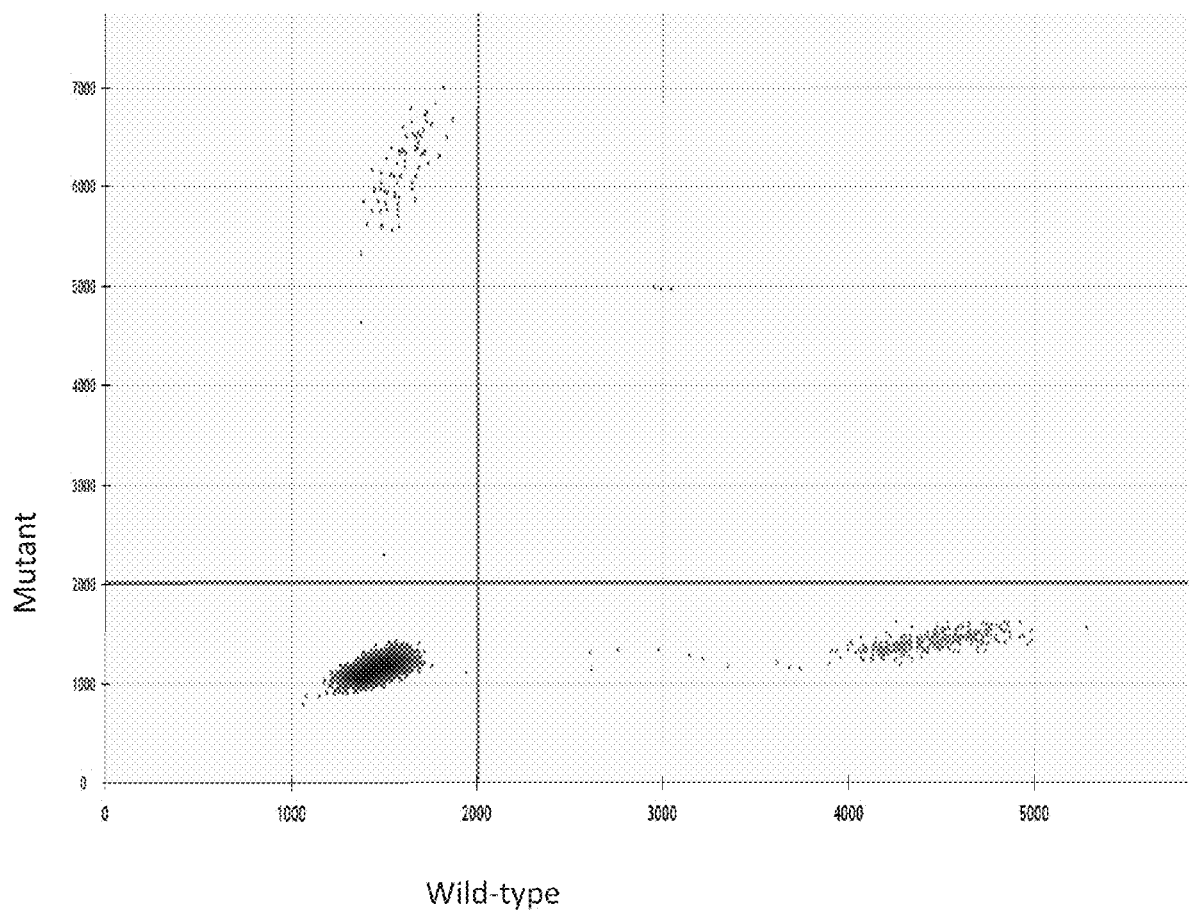
Figure 8F:
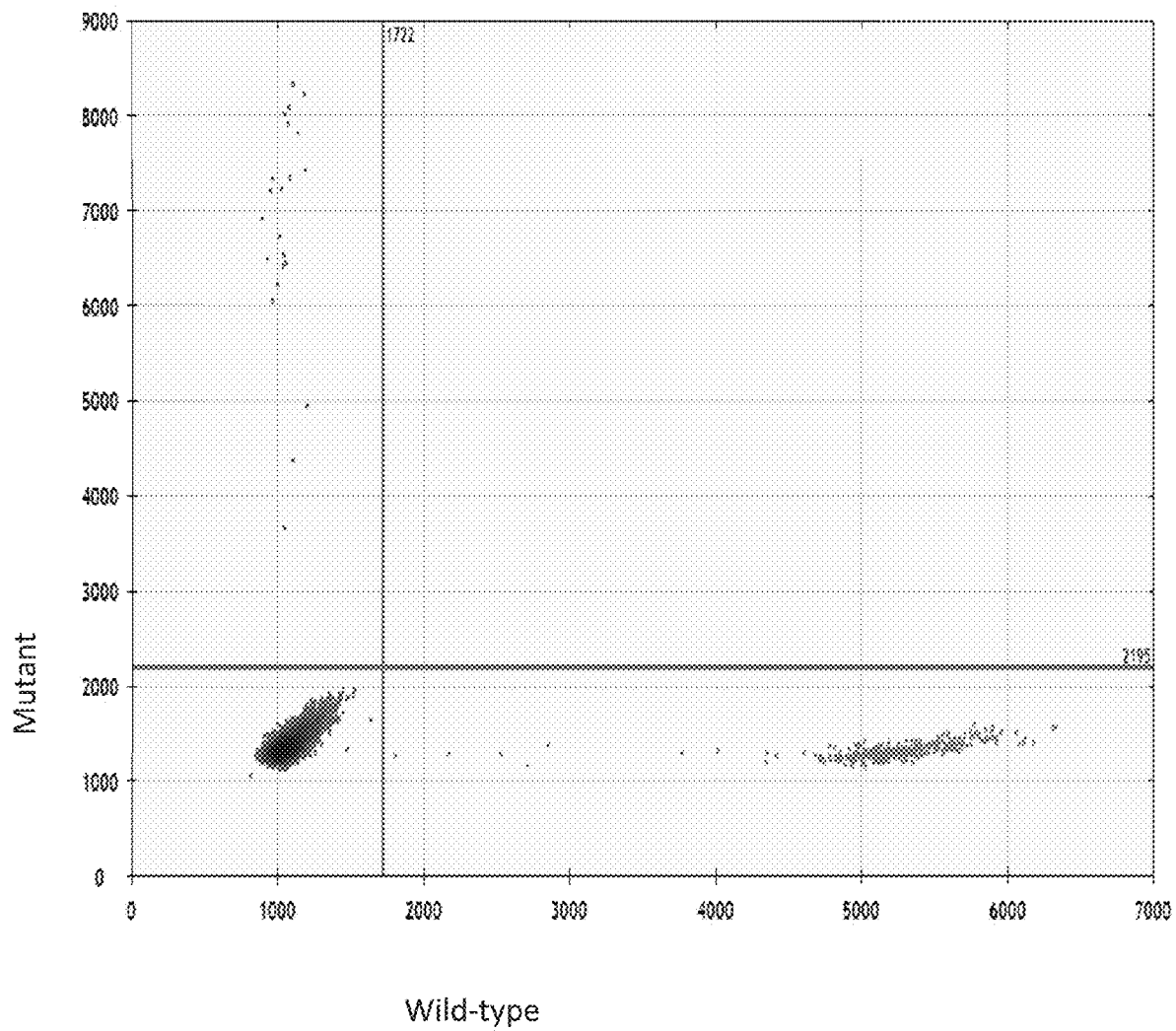
Figure 8G:
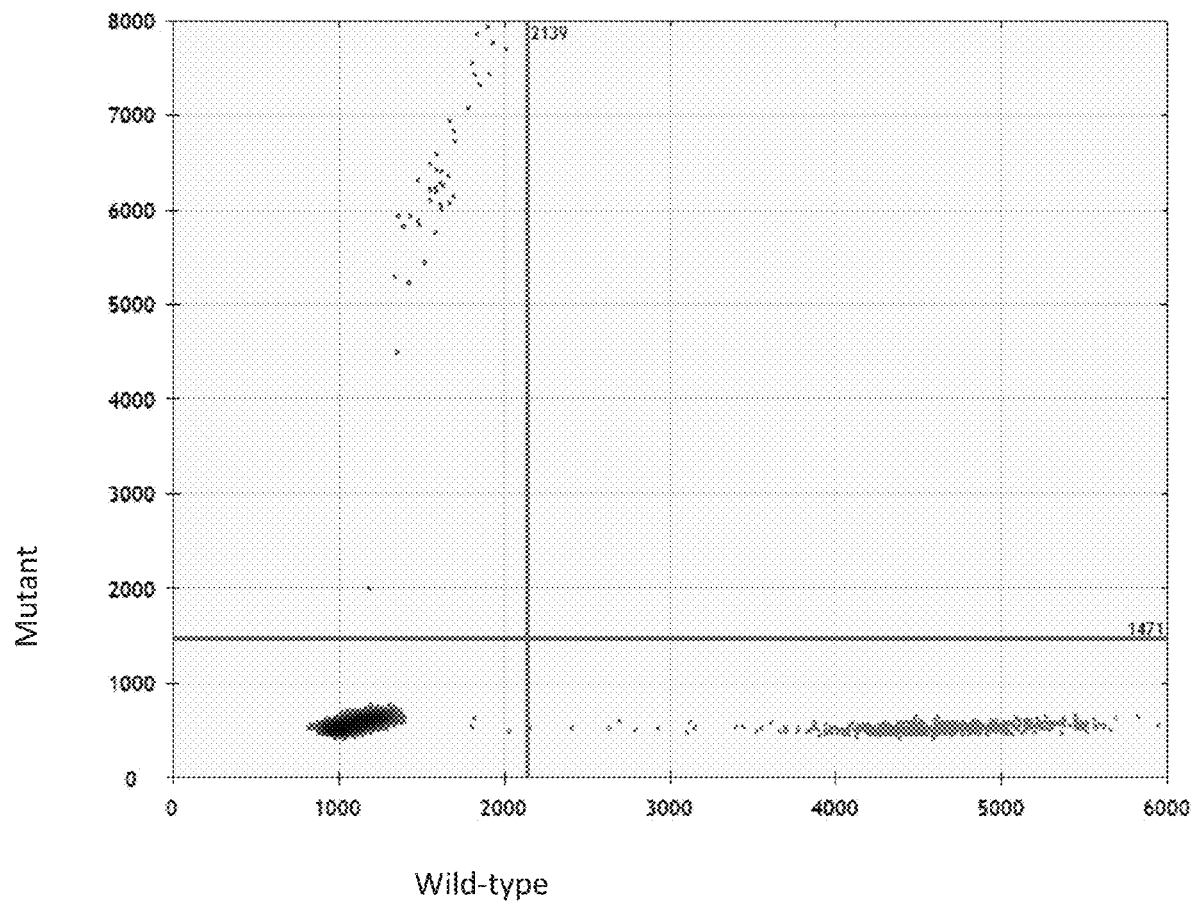
Figure 8H:
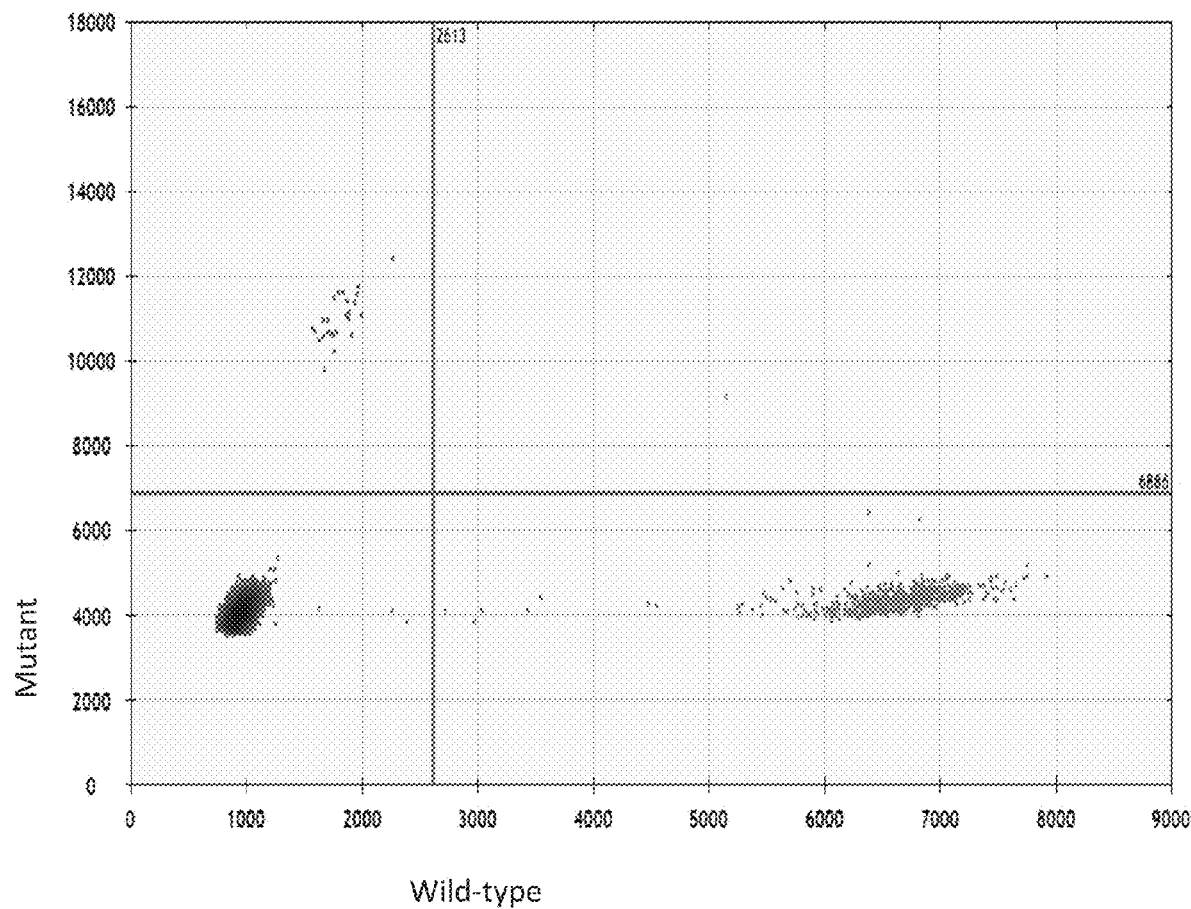
Figure 8I:
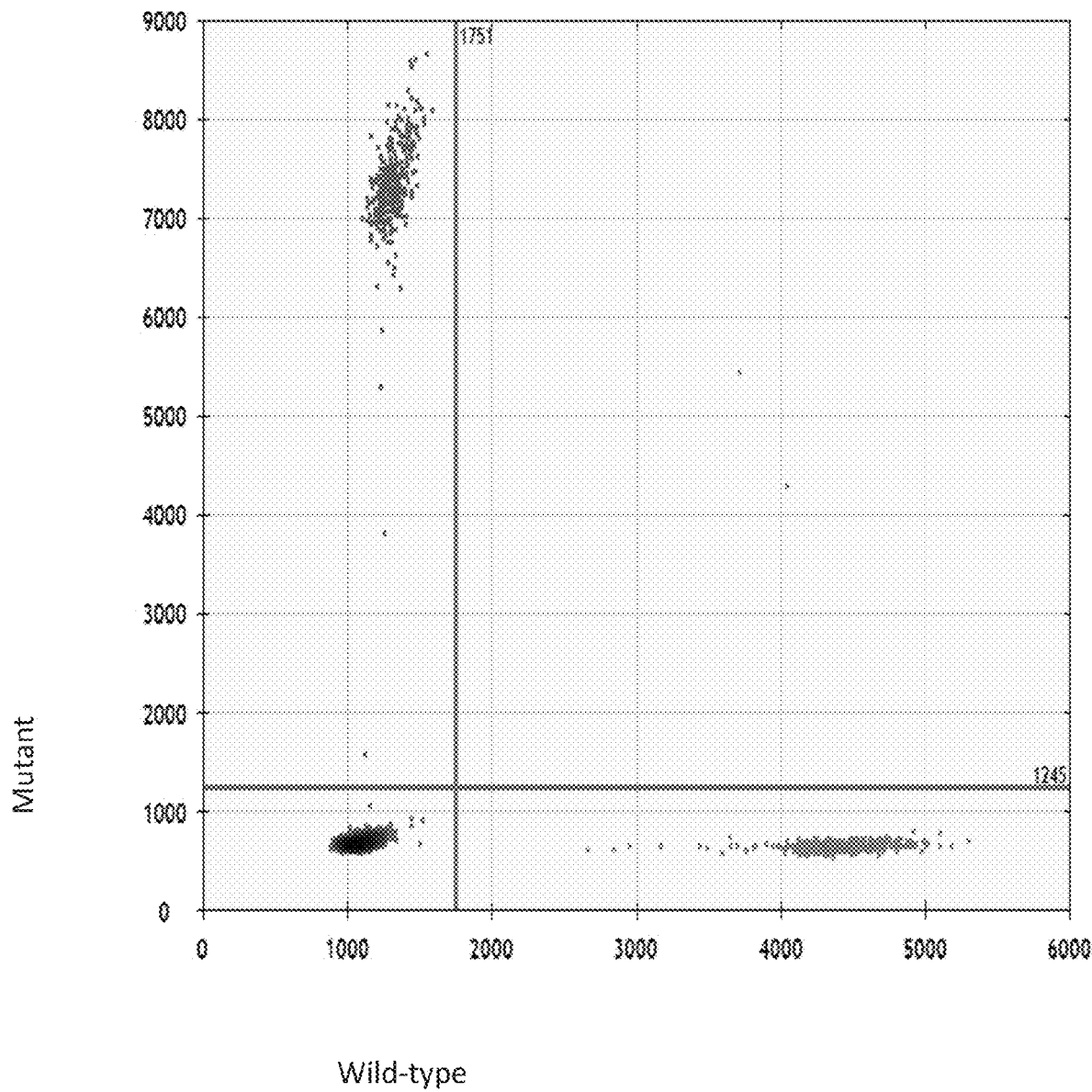
Figure 8J:
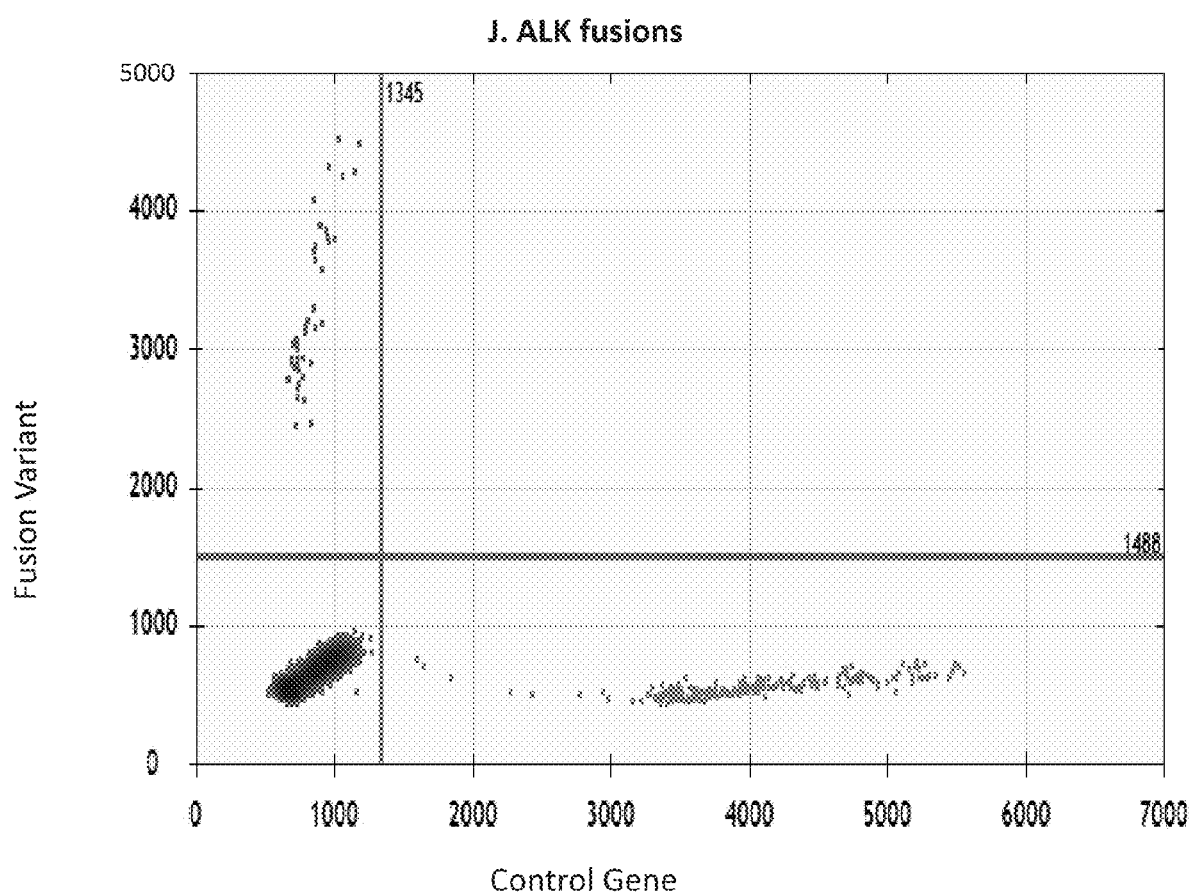
Figure 8K:
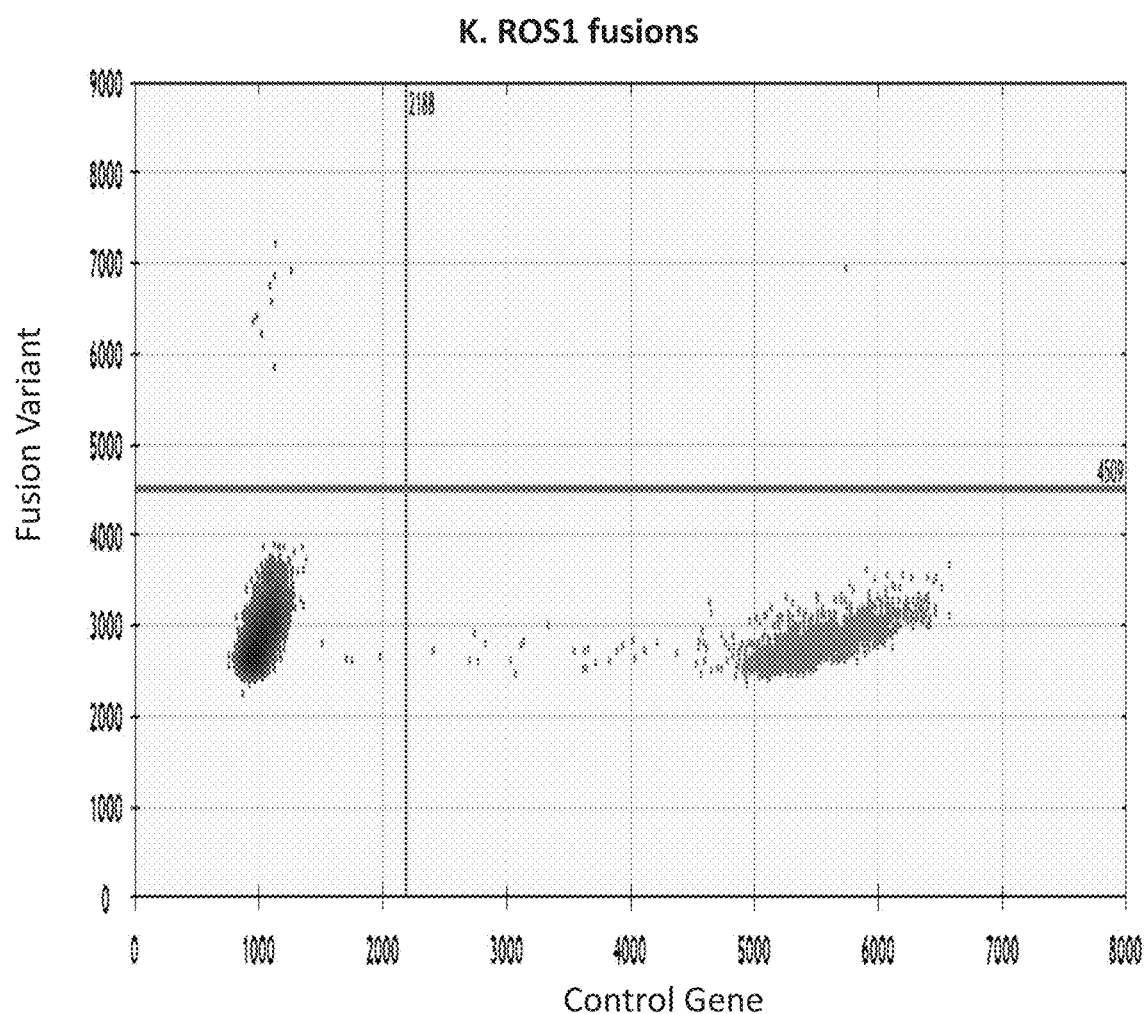
Figure 8L:
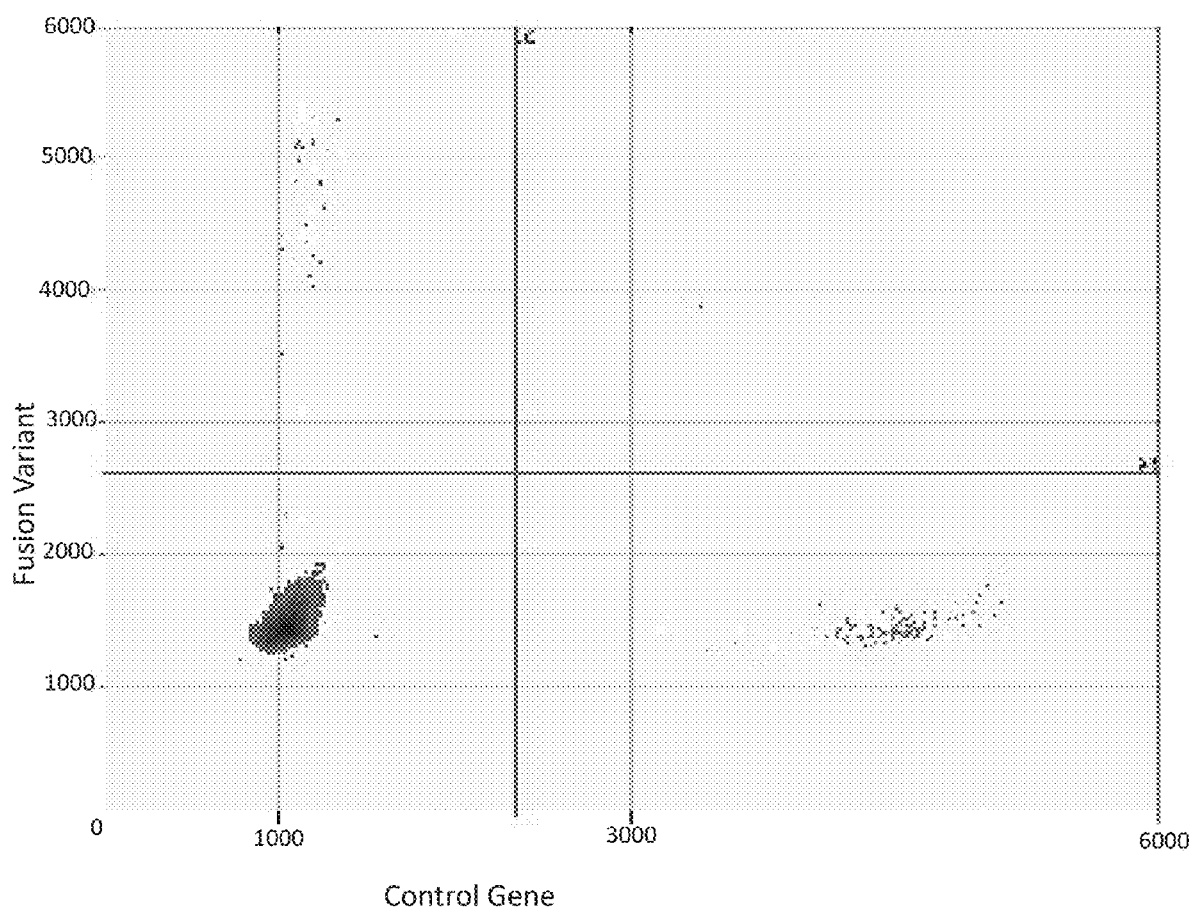
Figure 8M:
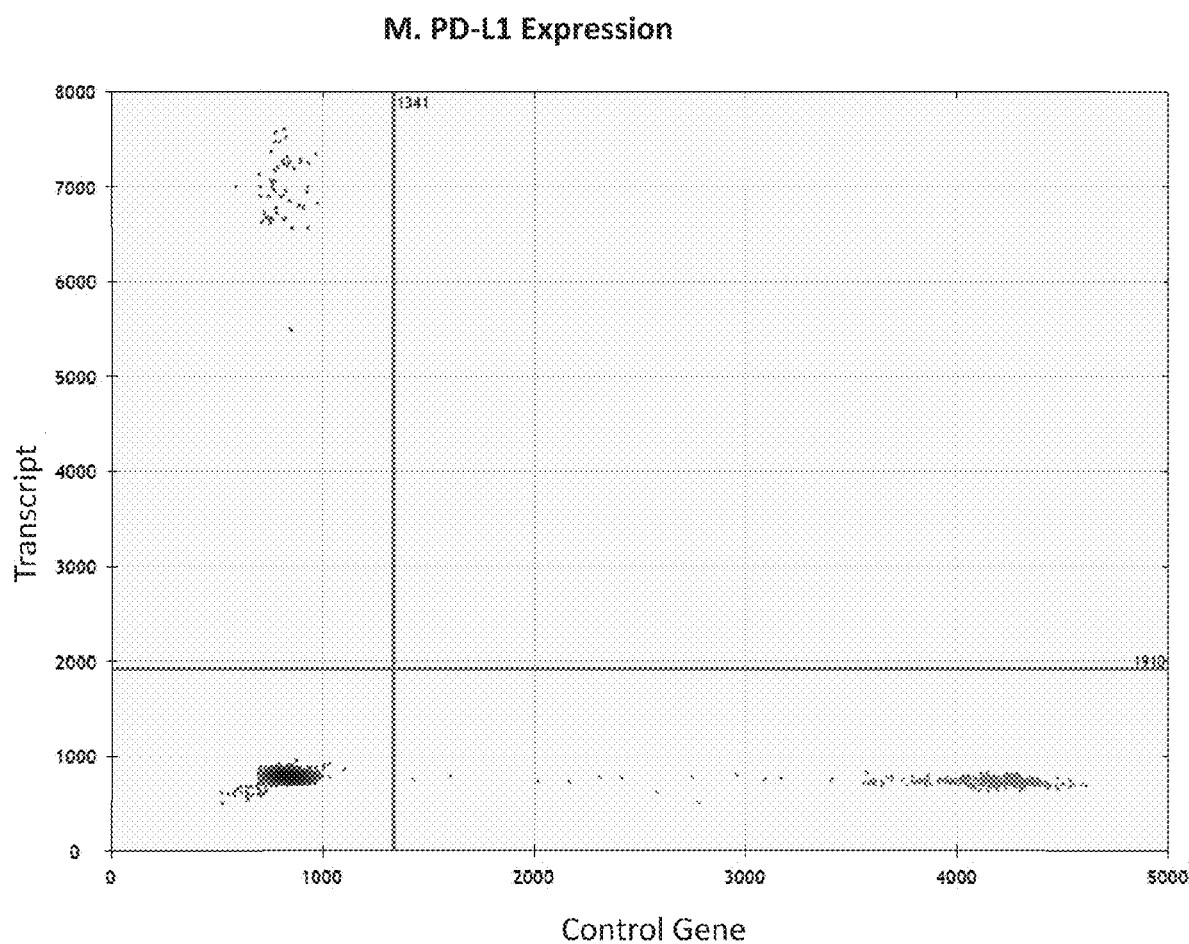

The control gene in this experiment was GUSB. The single variant positive droplet detected in the 0.2% conditions are indicated with arrows.

FIGS. 15A-C. RT-ddPCR and qPCR can be used to assess gene expression in multiple cell types. Four lung cancer cell lines, four PBMC fractions, and nine normal human PBMC samples were tested for PD-L1 (CD274, Bio-Rad) by (FIG. 15A) qPCR and (FIG. 15B) ddPCR amplification methods. (FIG. 15C) ddPCR and qPCR expression levels were equivalent ($R^2$=0.9835). ddPCR results are shown as absolute copy number and qPCR data is shown as expression relative to the highest-expressing sample.

FIGS. 16A-D. The GeneStrat® Test System used to assess gene expression from PEP. Twenty blood samples were collected from cancer patients that were either (FIGS. 16A-16C) wild-type for EGFR (EGFRwt) or (FIGS. 16C-16F) EGFR-sensitizing mutation positive (EGFR L858R or ΔE746-A750). Expression analysis was performed using ddPCR for either (FIGS. 16A-D) the mRNA transcript that codes for the immune checkpoint inhibitor PD-L or (FIGS. 16B-E) the mRNA transcript that codes for the epithelial marker CK19. The ratio of PD-L expression to CK19 expression is shown in 16C and 16F.

FIGS. 17A-E. Precision of GeneStrat® Test System. (FIG. 17A) Variant assays were evaluated by ddPCR at Horizon Discovery with a pre-qualified standard of known % MVF. The same standards were evaluated at Biodesix using the QX200 ddPCR system. Note: EML4-ALK was not evaluated in the study. (FIG. 17B) Intra-run studies for each EGFR and KRAS variant were run with three cancer donor plasma samples or, in the case of L858R, using analytic cell-line standards (Horizon Discovery). The mean % MVF is represented ±S.D. for the three independent runs. (FIG. 17C) Intra-run studies for the EML4-ALK multiplexed assay was run with three concentrations of analytic RNA standard. The mean number of copies is represented ±S.D. for the three independent runs. (FIG. 17D) Inter-run studies for EGFR and KRAS were performed as in B. except that the mean±S.D. represents runs on three consecutive days of testing. (FIG. 17E) Inter-day testing of the EML-ALK assay was performed as in C. except that the mean±S.D. represents runs on three consecutive days of testing.

FIGS. 18A-C. Robustness of GeneStrat® Test System. Analytic positive control was spiked into normal human plasma, extracted, and tested by ddPCR over 21 consecutive business days. Both mutant and wild-type copies are reported in FIG. 18A. EGFR ΔE746-A750, EGFR L858R, and EGFR T790M, and FIG. 18B. KRAS G12C, KRAS G12D, and KRAS G12V. FIG. 18C show EML4-ALK fusion copies and control gene copies detected using the EML4-ALK multiplex for detection of variant 1, 2 and 3.

FIGS. 19A-B. Test Request From and Test Result Report Forms. (FIG. 19A) An electronic individualized patient specific Test Request Form (TRF) and (FIG. 19B) an electronic Test Result Reports (TRR) that integrates physician, patient, reimbursement, treatment impact, communicates the VeriStrat® protein signature label and the molecular test result is generated by the test system.

FIGS. 20A-C. CK19 and PD-L1 Detection by RT-ddPCR in a Lung Cancer Cell Line. Cytokeratin and PD-L1 expression were assessed simultaneously in the NCI-H226 cell line using a multiplexed ddPCR assay. Quantasoft 2D Plots are shown in FIG. 22A, and the gDNA and ddPCR Controls are shown in FIGS. 22B-C, respectively. gDNA Control: No reverse transcriptase was included in the reverse transcription reaction. ddPCR Control: ddPCR reaction assembled without cDNA.

Figure 21:
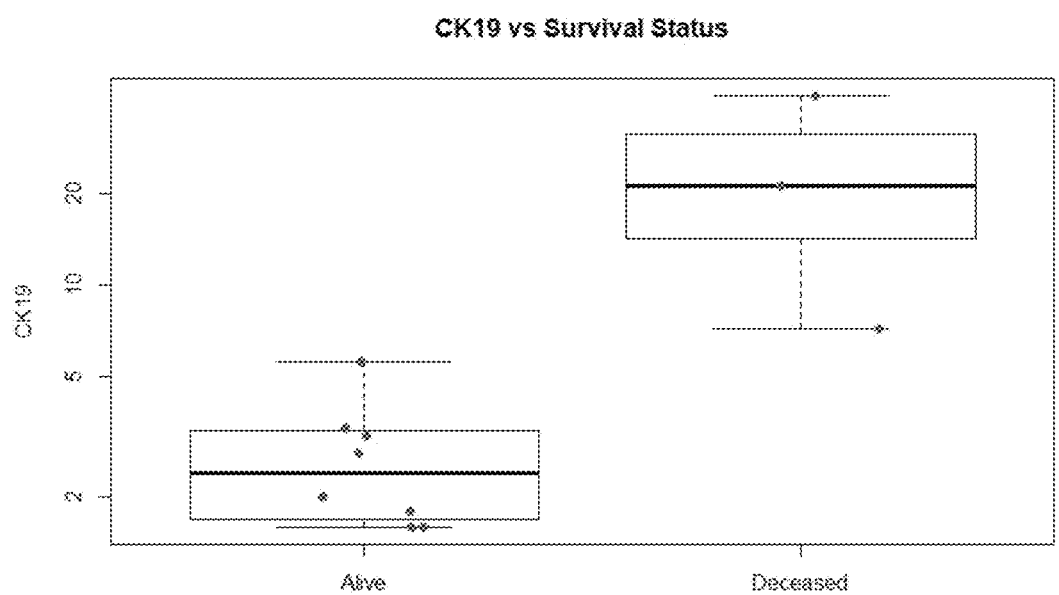

FIG. 21. Boxplots Comparing the CK19 Values of Deceased Subjects v. Still Alive. The inventors observed that the three deceased patients had the highest levels of circulating CK19. These data indicate a poor prognostic role associated with elevated levels of circulating CK19 mRNA in cancer progression and patient survival.

Figure 22:
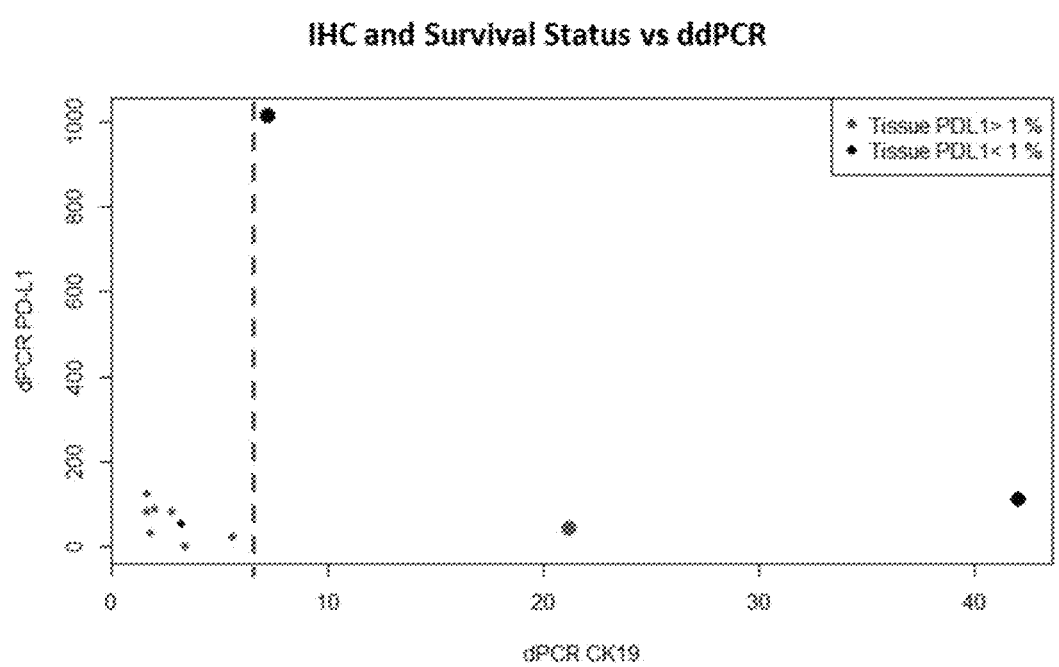

FIG. 22. A 4-Way View of the Available Data. dPCR CK19 (X-axis), dPCR PD-L1, IHC PD-L1 (dot color), and Survival Status (dot size: large=deceased, small=alive). Aside from the poor prognostic value associated with elevated levels of CK19 (all of the 3 larger dots are on the right side of the vertical line) which was observed in FIG. 20 above, the inventors did not observe any further potential associations with the PD-L1 biomarker at this time.

Figure 23:
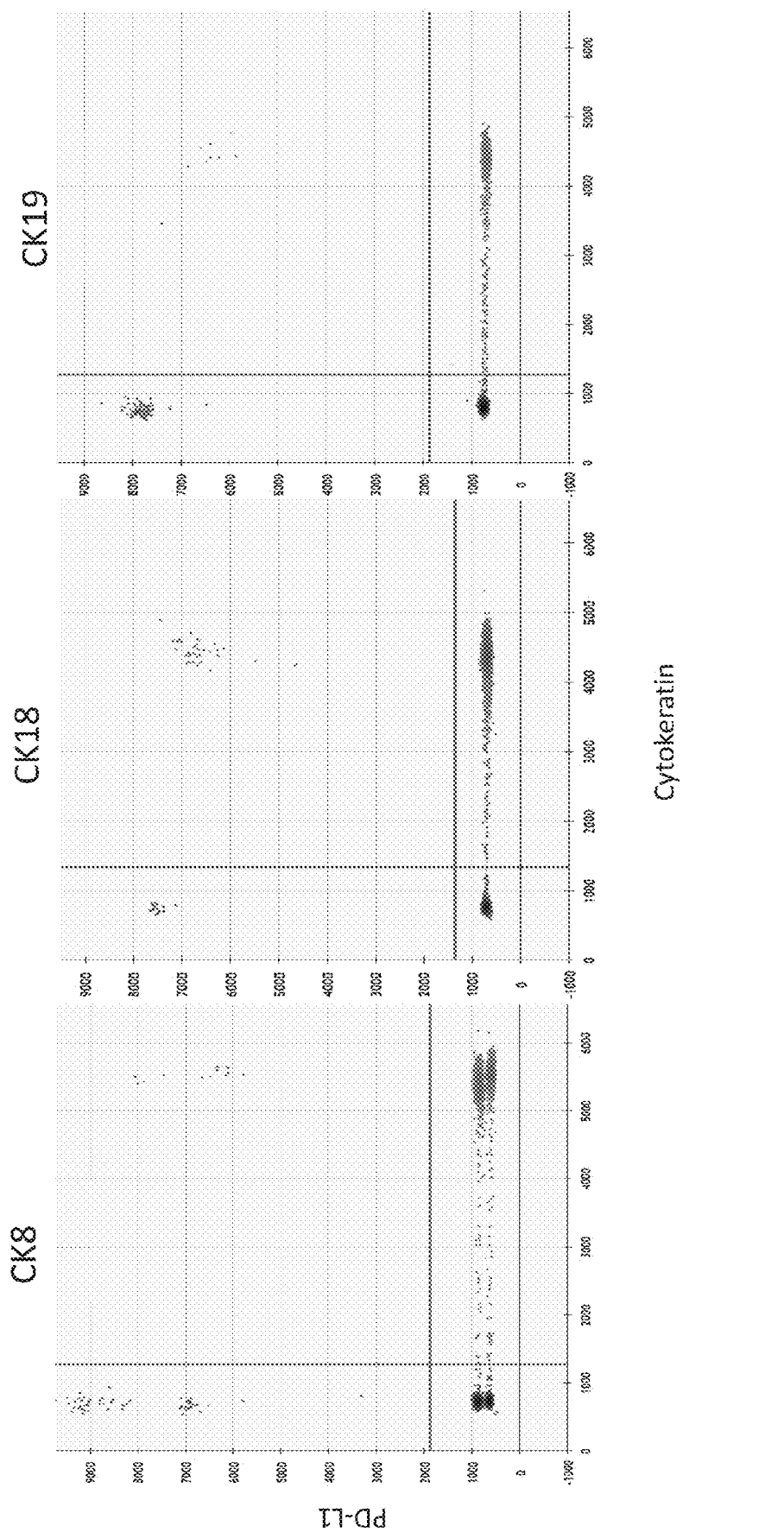

FIG. 23. RT-ddPCR Detection of Cytokeratin Expression in a Lung Cancer Cell Line. Cytokeratin and PD-L1 expression were assessed in the NCI-H226 cell line using multiplexed ddPCR assays. Quantasoft 2D Plots are shown for PD-L1 multiplexed with CK8, CK18, or CK19.

DETAILED DESCRIPTION

In their research, the inventors focused on the development of a diagnostic test system (FIGS. 1A-F) that includes the prospective collection of whole blood, preservation of circulating nucleic acids at ambient temperature, and the reproducible detection of nucleic acids including DNA and mRNA (including fusion transcripts and differentially expressed transcripts) by different genomic methodologies. Specifically, the inventors have focused on the examination of mRNA transcripts and somatic DNA mutations and indels in whole blood from donors with and without previously diagnosed cancer.

Pre-analytic complexity is the most confounding parameter in the development of molecular diagnostic tests since many of the parameters are beyond the control of laboratories charged with the day to day performance of these tests. Here, the inventors have reduced the impact of this variable by design of simple and controlled procedures embodied in a specimen collection kit for the collection and shipment of human blood donor samples (FIGS. 2A-L). First, they utilized specific blood collection reagents at the time of draw. These blood collection tubes (DNA and RNA blood collection tubes, examples are from Streck Inc. NE; FIGS. 1B-C) specifically protect white blood-cell membranes from lysis during shipment, and thus reduce contamination of circulating nucleic acids in the cell-free compartment (FIGS. 3A-B). In the case of the RNA blood collection tubes, inhibitors of RNAse enzymes are also included by the manufacturer that reduce circulating RNA degradation (FIG. 4). The inventors further stabilized the performance of the blood collection tubes by including specific packaging that maintains ambient temperatures in the blood samples during shipping (FIG. 2E). Finally, they controlled the time in transit of samples by utilizing priority overnight shipping and pick-up for all samples coming to the testing laboratory. On arrival at the laboratory, trained personnel handle sample processing of blood to isolate components being subjected to analysis for nucleic acid detection. A key requirement for producing reproducible results in this diagnostic test system is to restrict the handling of samples to 72 hours from time of sample receipt in the Laboratory to the generation of the test result.

In demonstrating the advantages of the disclosed system, the inventors focused on actionable molecular targets in advanced NSCLC including the DNA somatic variants, EGFR L858R, exon 19 deletion (ΔE746-A750) and T790M, KRAS G12C/D/V and BRAF V600E; mRNA fusion transcripts including EML4-ALK, ROS1 and RET; and overexpressed mRNA transcripts, including PD-L1 (FIGS. 1A-F). As examples, test development included method and clinical validation using samples from normal and cancer donors for EGFR sensitizing, resistance, KRAS and EML4-ALK fusions (FIGS. 5A-C). Clinical sensitivity and specificity were established for each variant, with a range of 85-100%/o and 100%, respectively. The inventors also report here on over 1000 NSCLC samples processed within the inventors' CLIA-certified Laboratory. Samples were run from patients previously diagnosed with Lung, Breast, Head and Neck as well as other cancer types (FIG. 6A). Mutation results were available within 72 hours for 94% of the tests evaluated (FIG. 6B). The percentage of samples for which the inventors have detected mutations are 10.5% for EGFR sensitive (n=2801 variants tested), 13.8% for EGFR resistant (n=1055), 13.2% for KRAS (n=3477) and 2% for EML4-ALK fusions (n=304) (FIGS. 7A-B).

Thus, the system and methods disclosed herein are highly suited for rapid, reproducible and sensitive detection of diagnostic nucleic variants, including mRNA fusions, mRNA transcripts that may be differentially expressed and somatic DNA mutation variants. The procedure may be transferrable using this test service in other clinical laboratories. These and other aspects of the disclosure are set out in detail below.

I. Test Detection System

The detection system utilized in the studies below is based on droplet digital PCR (ddPCR), which was optimized for rare mutation detection (RMD) from blood. ddPCR is a highly sensitive gene mutation detection method that is based on the partitioning of DNA into droplets (Hindson et al., 2011). There are now several ddPCR assays that have been developed for various common and rare cancer mutations; these assays have demonstrated the utility of the technology in the clinic (Sacher et al., 2016; Oxnard et al., 2014; Beaver et al., 2014; Takeshita et al., 2015). The inventors used several specimen types and included synthetic DNA oligonucleotides, cell line (e.g., tumor) derived RNA and DNA, cell line materials spiked into normal plasma, as well as circulating nucleic acids isolated from normal and cancer donor whole blood samples while developing these tests. In the EGFR, KRAS and BRAF RMD tests, the inventors determined the presence of DNA somatic variants and the relevant wild-type sequences in dual detection assays. In the case of the gene-fusion assays (EML4-ALK, ROS1 and RET), cDNA copied from the plasma derived RNA was measured in a multiplexed format. In the case of mRNA transcript overexpression using ddPCR, the inventors' assays measured mRNA expression in PEP from normal, healthy donors, as well as cancer donors harboring variable levels of PD-L1 transcripts. Relative expression as compared to cancer specific control genes including cytokeratin 19 is also described for this latter use of the diagnostic test system. Assay information used for the various variants are listed in the Tables.

II. Specimen Collection Kit

A specimen collection kit (SCK) is optimized for the collection and shipment of whole blood samples used for nucleic acid recovery, and for serum samples on a dried blood spot cards used for protein recovery (FIGS. 2A-L). Critical components of the kit that enable the stable recovery of plasma and PEP include DNA and RNA blood collection tubes, packs for maintaining ambient temperatures of the whole blood samples, as well as packaging for protecting samples from breakage and spills.

III. PCR Technology

A. Digital PCR

Digital PCR (dPCR) is used for identification of predefined mutations or rare variants of nucleic acids in a background of common sequences expected to be present in a minor fraction of a cell population. Using partitioning of the PCR reaction, the exponential nature of PCR amplification is transformed into a linear, digital signal. Single molecules are isolated and individually amplified; each product is then separately analyzed for the presence of pre-defined mutations. The process provides a reliable and absolute quantitative measure of the proportion of variant sequences within a DNA sample (see U.S. Pat. No. 7,824,889, incorporated herein by reference). Digital PCR is now known in the art to include methods of patriations including, but not limited to the following:

i. ddPCR

Droplet Digital PCR (ddPCR) is a method for performing digital PCR that is based on water-oil emulsion droplet technology that uses microfluidics. A sample is fractionated into 20,000 droplets, and PCR amplification of the template molecules occurs in each individual droplet. ddPCR technology uses reagents and workflows similar to those used for most standard TaqMan probe-based assays. The massive sample partitioning is a key aspect of the ddPCR technique (U.S. Pat. RE 43,365 E1, incorporated herein by reference).

The Droplet Digital PCR System partitions nucleic acid samples into thousands of nanoliter-sized droplets, and PCR amplification is carried out within each droplet. This technique has a smaller sample requirement than other commercially available digital PCR systems, reducing cost and preserving precious samples.

In traditional PCR, a single sample offers only a single measurement, but in Droplet Digital PCR, the sample is partitioned into 20,000 nanoliter-sized droplets. This partitioning enables the measurement of thousands of independent amplification events within a single sample.

ddPCR technology uses a combination of microfluidics and proprietary surfactant chemistries to divide PCR samples into water-in-oil droplets (Hindson et al., 2011). The droplets support PCR amplification of the template molecules they contain and use reagents and workflows similar to those used for most standard TaqMan probe-based assays. Following PCR, each droplet is analyzed or read in a flow cytometer-like instrument to determine the fraction of PCR-positive droplets in the original sample. These data are then analyzed using Poisson statistics to determine the absolute number of target DNA template within in the original sample.

Droplet Digital PCR surpasses the performance of earlier digital PCR techniques by resolving the previous lack of scalable and practical technologies for digital PCR implementation. Serial dilution is laborious and introduces the potential for pipetting error; competing chip-based systems rely on complex fluidics schemes for partitioning. Droplet Digital PCR addresses these shortcomings by massively partitioning the sample in the fluid phase in one step. The creation of tens of thousands of droplets means that a single sample can generate tens of thousands of data points rather than a single result, bringing the power of statistical analysis inherent in digital PCR into practical application. Bio-Rad's Droplet Digital PCR System® automates the ddPCR workflow of droplet generation, thermal cycling, droplet reading, and data analysis.

ddPCR reactions (PrimePCR; BioRad. FIG. 1D) were set up in duplicate. Each reaction well was mixed to a final volume of 20 µl with the following: 10 µl of 2× ddPCR Supermix for probes, no dUTP, 1 µl of 20× variant target primers/probe set (450 nM primers/250 nM FAM probe), 1 µl of 20× control target primers/probe set (450 nM primers/250 nM HEX probe), and up to 7 µl of the test template DNA (cfDNA or cDNA). Restriction digestion of template DNA was executed within the PCR mix by adding 2-5 units of enzyme (Hind III, Alu I, Mse I) per ng of DNA. Hind III was used for EGFR T790M and L858R; Alu I for EGFR ΔE746-A750 and Mse I for all KRAS assays (New England BioLabs). The gene fusion assays do not include restriction enzymes. No template control (NTC) reactions were performed with pure double-distilled water in place of the DNA template and were run with every assay within a plate (Mellert et al., 2017, in press). Examples for 2D plots for all variants are shown in FIGS. 8A-M.

Droplet generation was performed with either a manual or automated droplet generation QX200 system (BioRad) according to the manufacturer's guidelines. Once emulsions were generated, plates were placed into a C1000 Touch thermal cycler (BioRad). The thermal cycling profile was optimized as follows: 95° C., 10 min (enzyme activation, 1 cycle) followed by denaturation (94° C., 30 sec) and annealing/extension (55° C., 1 min), ramp rate of ~2° C./sec; 40 cycles. To conclude the procedure, enzyme deactivation was done at 98° C., 10 min followed by hold at 4° C. (ramp rate of ~1° C./sec). After amplification, the plate was transferred to the droplet reader (BioRad). Samples were read using the Rare Event Detection module on the reader (QuantaSoft™ ver., 1.7.4.0917).

ii. Other Digital PCR Methods

Other digital PCR technologies that include but are not limited to RainDrop PCR, an ultra-sensitive platform for nucleic acid detection that provides absolute quantification of specific targets by partitioning a standard quantitative PCR reaction into millions of individual picoliter droplets and Crystal Digital PCR, which relies on the use of a single chip to partition samples into 2D droplet arrays, which are then subjected to thermal cycling and finally read using a three-color fluorescence scanning device.

B. Non-Partitioned PCR i. End-Point PCR

Conventional PCR is also referred to as end-point PCR. The results of a PCR reaction that amplifies many targets within the same reaction is visualized on a gel once the run has finished. End-Point PCR is not quantitative, which distinguishes it from real-time or Quantitative PCR.

ii. Quantitative PCR

Quantitative PCR is a method of monitoring amplification during a PCR reaction in real-time. The method uses fluorescence in the form of labelled probes or intercalating dyes to monitor the quantity of amplified product.

IV. Data Analysis, Review and Result Generation

Data review and analysis were conducted to determine negative and positive droplet counts for each sample using the QuantaSoft analysis modules. For calculating mutant and wild-type copy numbers for DNA mutation tests (FIG. 8A-I), two or more variant copies were required to call a sample positive and 300 or more copies were required to call a negative result. The DNA-variant tests (EGFR and KRAS) results were either expressed as number of copies or by the percent minor variant frequency (% MVF) of the mutation in relation to wildtype. The clinical cut-off for calling a positive sample in the validation studies was defined at 0.02% MVF. Variant frequencies were calculated as follows:

$$\% \ MVF = \frac{\text{Mutation Copy Number}}{\text{Mutation} + WT \ \text{Copy Number}} * 100$$

For calculating RNA tests the GUSB or CK19 control transcripts were used as assay quality controls to verify the presence of circulating nucleic acids of sufficient quality and quantity for testing (FIGS. 8J-M). For RNA fusions tests the clinical cut-off for validation studies was defined at 2 or more copies of fusion variant. In the case of PD-L1 expression testing the clinical cutoff was 30 of more copies of PD-L1.

V. Somatic DNA Variants

Somatic DNA variants, including rearrangements, point mutations and indels, are critical alterations that influence malignant transformation and ultimately may result in disease progression. The clinical significance and importance of aberrations in the epidermal growth factor receptor (EGFR), Kirsten ras (KRAS) and BRAF have been previously reported (Weber et al., 2014; Lynch et al., 2004; Paez et al., 2004; Pao et al., 2004; Yu et al., 2013). Identification of the "driver" genomic alterations (oncogenic drivers) and targeting those specific alterations with therapy are critical aspects of today's approach to the management of cancer (Sahnane et al., 2016; Paxton, A., 2014). The epidermal growth factor receptor (EGFR) gene is estimated to be mutated in 10-40% of patients with NSCLC (Salgia, R., 2015). Approximately 90% of these EGFR mutations occur in either exon 19 from amino acids E746-A750 or as an amino acid substitution in exon 21 at codon 858 (L858R) (Yu et al., 2009), both of which confer sensitivity to the EGFR tyrosine kinase inhibitors (TKIs) IRESSA® (gefitinib), TARCEVA® (erlotinib), and GILOTRIF® (afatinib). The EGFR exon 20 mutation T790M is the most commonly recognized mechanism of drug resistance to these first-line EGFR tyrosine kinase inhibitors accounting for nearly 50% of the acquired resistance (Janne et al., 2015; Watanabe et al., 2015). T790M, initially considered as relevant only as a resistance marker is also now actionable with the regulatory approval of TAGRISSO® (osimertinib) for use in EGFR T790M mutation-positive NSCLC. BRAF is a human gene that encodes a protein called B-Raf. The gene is also referred to as proto-oncogene B-Raf and v-Raf murine sarcoma viral oncogene homolog B, while the protein is more formally known as serine/threonine-protein kinase B-Raf (Sithanandam et al., 1990; 1992). The B-Raf protein is involved in sending signals inside cells which are involved in directing cell growth. In 2002, it was shown to be faulty (mutated) in some human cancers (Davies et al., 2002). FDA approved therapies that treat cancers driven by BRAF mutations have been developed. Specifically, including vemurafenib and dabrafenib are approved by FDA for treatment of late-stage melanoma.

VI. Keratins

Keratin is one of a family of fibrous structural proteins. It is the key structural material making up hair, horns, claws, hooves, and the outer layer of human skin. Keratin is also the protein that protects epithelial cells from damage or stress. Keratin is extremely insoluble in water and organic solvents. Keratin monomers assemble into bundles to form intermediate filaments, which are tough and form strong unmineralized epidermal appendages found in reptiles, birds, amphibians, and mammals.

Cytokeratins are keratin proteins found in the intracytoplasmic cytoskeleton of epithelial tissue. They are an important component of intermediate filaments, which help cells resist mechanical stress. Expression of these cytokeratins within epithelial cells is largely specific to particular organs or tissues. Thus they are used clinically to identify the cell of origin of various human tumors. The term "cytokeratin" began to be used in the late 1970s, when the protein subunits of keratin intermediate filaments inside cells were first being identified and characterized. In 2006 a new systematic nomenclature for mammalian keratins was created, and the proteins previously called "cytokeratins" are simply called keratins (human epithelial category). For example, cytokeratin-4 (CK-4) has been renamed keratin-4 (K4). However, they are still commonly referred to as cytokeratins in clinical practice.

There are two categories of cytokeratins: the acidic type I cytokeratins and the basic or neutral type II cytokeratins. Within each category, cytokeratins are numbered in order of decreasing size, from low molecular weight (LMWCKs) to high molecular weight (HMWCKs). Cytokeratins are usually found in heterodimeric pairs of acidic and basic subunits of similar size. The basic/HMWCK cytokeratins are CK-1 through -6, the acidic/HMWCK cytokeratins are CK-9 through -17, the basic/LMWCK cytokeratins are CK-7 and CK-8, and the acidic/LMWCK cytokeratins are CK-18 through -20.

Expression of these cytokeratins is largely organ or tissue specific. The subsets of cytokeratins which an epithelial cell expresses depends mainly on the type of epithelium, the moment in the course of terminal differentiation and the stage of development. Thus a specific cytokeratin expression profile allows the identification of epithelial cells. Furthermore, this applies also to the malignant counterparts of the epithelia, (carcinomas), as the cytokeratin profile is generally retained. Thus the study of cytokeratin expression by immunohistochemistry techniques is a tool of immense value widely used for tumor diagnosis and characterization in surgical pathology.

TABLE A

| Cytokeratin | Sites |
|---|---|
| Cytokeratin 4 | Non-keratinized squamous epithelium, including cornea and transitional epithelium |
| Cytokeratin 7 | A subgroup of glandular epithelia and their tumors Transitional epithelium and transitional carcinoma |
| Cytokeratin 8 | Glandular epithelia of the digestive, respiratory and urogenital tracts, both endocrine and exocrine cells, as well as mesothelial cells Adenocarcinomas originating from those above |
| Cytokeratin 10 | Keratinized stratified epithelium Differentiated areas of highly differentiated squamous cell carcinomas |
| Cytokeratin 13 | Non-keratinized squamous epithelia, except cornea |
| Cytokeratin 14 | Basal layer of stratified and combined epithelia |
| Cytokeratin 18 | Glandular epithelia of the digestive, respiratory, and urogenital tracts, both endocrine and exocrine cells, as well as mesothelial cells Adenocarcinomas originating from those above |
| Cytokeratin 19 | Glandular-type epithelia, carcinomas; does not react with hepatocytes and hepatocellular carcinoma |
| Cytokeratin 20 | Glandular-type epithelia. Signet ring/round clear cells GI stromal tumor (Krukenberg) |

The cytokeratins are encoded by a family encompassing 30 genes. Among them, 20 are epithelial genes and the remaining 10 are specific for trichocytes.

All cytokeratin chains are composed of a central α-helix-rich domain (with a 50-90% sequence identity among cytokeratins of the same type and around 30% between cytokeratins of different type) with non-α-helical N- and C-terminal domains. The α-helical domain has 310-150 amino acids and comprises four segments in which a seven-residue pattern repeats. Into this repeated pattern, the first and fourth residues are hydrophobic and the charged residues show alternate positive and negative polarity, resulting in the polar residues being located on one side of the helix. This central domain of the chain provides the molecular alignment in the keratin structure and makes the chains form coiled dimers in solution.

The end-domain sequences of type I and II cytokeratin chains contain in both sides of the rod domain the subdomains V1 and V2, which have variable size and sequence. The type II also presents the conserved subdomains H1 and H2, encompassing 36 and 20 residues respectively. The subdomains V1 and V2 contain residues enriched by glycines and/or serines, the former providing the cytokeratin chain a strong insoluble character and facilitating the interaction with other molecules. These terminal domains are also important in the defining the function of the cytokeratin chain characteristic of a particular epithelial cell type.

Two dimers of cytokeratin groups into a keratin tetramer by anti-parallel binding. This cytokeratin tetramer is considered to be the main building block of the cytokeratin chain. By head-to-tail linking of the cytokeratin tetramers, the protofilaments are originated, which in turn intertwine in pairs to form protofibrils. Four protofibrils give place to one cytokeratin filament. In the cytoplasm, the keratin filaments conform a complex network which extends from the surface of the nucleus to the cell membrane. Numerous accessory proteins are involved in the genesis and maintenance of such structure.

This association between the plasma membrane and the nuclear surface provides important implications for the organization of the cytoplasm and cellular communication mechanisms. Apart from the relatively static functions provided in terms of supporting the nucleus and providing tensile strength to the cell, the cytokeratin networks undergo rapid phosphate exchanges mediated depolymerization, with important implications in the more dynamic cellular processes such as mitosis and post-mitotic period, cell movement and differentiation.

Cytokeratins interact with desmosomes and hemidesmosomes, thus collaborating to cell-cell adhesion and basal cell-underlying connective tissue connection.

The intermediate filaments of the eukaryotic cytoskeleton, which the cytokeratins are one of its three components, have been probed to associate also with the ankyrin and spectrin complex protein network that underlies the cell membrane.

VII. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Recovery of cfDNA from Plasma.

Retrospectively and prospectively-collected samples were evaluated. Whole blood samples were prospectively collected into either Cell-Free DNA BCT® (Streck) or BD K$_2$ EDTA Vacutainer (lavender top) tubes. Samples collected into BD tubes were immediately processed by the collection sites to plasma and frozen before being sent to Biodesix. The methods for processing whole-blood to plasma on-site were per the manufacturer's instruction (room temperature at a speed of 1000 to 1300 RCF for 10 minutes in a swinging bucket centrifuge or 15 minutes in a fixed-angle centrifuge). Frozen plasma specimens were received and centrifuged at high speed (16000×g for 10 min at 4° C.). In those cases where whole blood was collected into the Cell-Free DNA BCT, samples were shipped overnight to the Biodesix CLIA Laboratory and processed to plasma first by centrifugation at low speed (1900×g for 10 min at 4° C.) followed by a high speed spin of the plasma fraction as described above.

cfDNA was isolated using the QIAamp Circulating Nucleic Acid Kit (Qiagen) according to the manufacturer's instruction. DNA was quantitated by Qubit dsDNA HS Assay Kit (Life Technologies/Thermo Fisher).

RNA Fusions.

To enable method development for sample processing to RNA, the inventors examined assay specificity and sensitivity with different detection technologies, including qRT-PCR (probes from Thermo Inc. and system from Roche Molecular Diagnostics), Anchored Multiplex PCR™ sequencing (AMP-specific reagents from ArcherDx Inc. and general reagents and miSeq instrument from Illumina Corp.) and RT-ddPCR (Droplet Digital™ PCR, BioRad Inc) (FIGS. 9A-B) Cell lines including EML4-ALK (Echinoderm Microtubule Associated Protein Like 4-Anaplastic Lymphoma Receptor Tyrosine Kinase), SLC34A2-ROS1 (Solute Carrier Family 34-ROS Proto-Oncogene 1) and CCDC6-RET (Coiled-Coil Domain Containing 6-Ret Proto-Oncogene) (Horizon Discovery Inc.), known to be positive for the respective RNA fusion transcripts were used to define specificity as well as limits of assay detection with the detection systems as applicable.

Recovery methods for RNA extraction from human donor whole blood samples were optimized to enrich for platelet-enriched plasma (PEP). PEPs represent unique samples that are enriched for RNA recovered from both circulating-free, or RNA bound and internalized within blood compartments, including platelets and exosomes. This RNA ranges in size from ~50-250 nucleotides (FIG. 10A). Plasma isolated from whole blood was processed to yield PEP (and described sub-components) using a combination of sequential centrifugation, silica slurries for nucleotide binding, and columns for filtration technologies. PEP was either snap-frozen at −80° C. or processed immediately to assess for mRNA fusions. One-step (RT and ddPCR) methods, as well as two-step (separate RT, nucleotide cleanup, followed by ddPCR) methods were evaluated in detection testing. To benchmark performance of the test system, the inventors used in vitro RNA transcripts spiked into normal human donor plasma, recovered RNA using the separation technologies as described above, and with the two-step RT/ddPCR detection, could detect as few as 24 copies of EML4-ALK fusion RNA (Mellert et al., 2017, in press). Six freshly collected donor plasma samples were processed from RNA blood collection tubes and processed for the recovery of RNA. In this test scenario, the inventors were able to measure the intended control (wild-type) RNA transcript in all tested samples (100%). They also detected the presence of as few as 12.8 copies KRAS (Kristen Rat Sarcoma Viral Oncogene Homolog) G12D RNA variant transcripts, and as few as 30 copies of a GUSB (Glucuronidase, Beta) wild-type control gene in different cancer specimens (Mellert et al., 2017, in press).

Recovery of Circulating RNA from Plasma.

Retrospectively procured samples were purchased as frozen plasma (Indivumed, GmbH). Prospectively procured whole blood samples were collected into Cell-Free RNA BCT. Multiple methods were evaluated for the recovery of circulating RNA (FIGS. 11A-F). The QIAmp method for extraction of circulating RNA from plasma was the most effective of the following four methods evaluated in these studies: QIAamp Circulating Nucleic Acid Kit (QIAmp, Qiagen), exoRNeasy Serum/Plasma Kit (ExoRNeasy, Qiagen), a trizol-based method (Trizol), and High Pure Viral Nucleic Acid Kit (Roche). In these experiments, blood samples were processed to plasma using a double centrifugation process. Samples were first centrifuged at 1900×g for 10 minutes, and the plasma supernatant was aspirated without disturbing the buffy coat layer. Cellular debris was then further removed by centrifugation at 16,000×g for 10 minutes. Approximately 3-5 ml plasma were obtained from one 10 ml whole blood collection tube. RNA yield was assessed using the Archer PreSeq RNA QC Assay Protocol (ArcherDx).

RNA yield from various whole blood compartments was then evaluated using differential centrifugation, and extraction methods were further assessed (FIGS. 11 D-F). PEP was prepared from whole blood by centrifugation at 200×g for 20 minutes. PDP (Platelet Depleted Plasma) and TEPs (Tumor Educated Platelets) were prepared by centrifugation of PEP at 360×g for 20 minutes. RNA was isolated and DNase-treated to remove genomic DNA using the Turbo DNA-free kit (ThermoFisher), and RNA was purified and concentrated using the Norgen RNA Clean-Up and Concentration Micro Kit. One-Step RT-ddPCR (Bio-Rad) was used to detect wild-type KRAS RNA as an indicator of RNA yield, and results are reported as absolute copy number for ddPCR reactions. The Norgen Plasma/Serum Circulating and Exosomal RNA Isolation Kit was able to extract RNA from TEPs (Tumor Educated Platelets) with high efficiency as compared to the mirVana miRNA Isolation Kit (Ambion) as well as from PEP, and the yield from PEP is equivalent to that of PDP plus TEPs from the same sample.

For the final assay, circulating RNA was isolated from PEP using the Plasma/Serum circulating and Exosomal RNA Purification Kit, slurry format (Norgen Biotek, Canada). Elution was performed into 100 µl of pre-warmed nuclease-free water and subsequently concentrated using the RNA Clean-Up and Concentration Kit (Norgen Biotek).

The inventors further evaluated the efficiency of conducting single tube, RT-ddPCR (OneStep) and the traditional two tube RT followed by ddPCR (FIGS. 12A-B). RNA that mimics the EML4-ALK fusion transcript (RNA that was transcribed in vitro from gBlock DNA sequences designed to match RNA variants 1, 2, and 3a) was spiked-in to normal human plasma post-lysis in the Norgen Plasma/Serum Circulating and Exosomal RNA Isolation Midi Kit. RNA was concentrated using the Norgen RNA Clean-Up and Concentration Micro Kit, and the sample was divided for assessment by RT-ddPCR by two methods in parallel. One-Step RT-ddPCR was conducted per manufacturer's instructions (Bio-Rad) while two-Step RT-ddPCR was performed using the Iscript cDNA Synthesis Kit (Bio-Rad). ddPCR results (QuantaSoft) are shown for EML4-ALK and the control gene, GUSB (FIGS. 12A-B). While both methods successfully detect EML4-ALK target cDNA, the ddPCR efficiency was improved using the two-step method and resulted in higher signal for positive droplets.

The inventors then evaluated the efficiency of using various RT enzymes along with traditional oligo-dT and random hexamers supplemented with various gene specific primers (GSP) (Tables 2A-B). EML4-ALK in vitro RNA was spiked into normal human plasma post-lysis in the Norgen Plasma/Serum Circulating and Exosomal RNA Isolation Midi Kit (Table 2A). RNA was concentrated using the Norgen RNA Clean-Up and Concentration Micro Kit, and cDNA was generated using either the Iscript Kit (Bio-Rad) or the Sensiscript Kit (Qiagen) with the addition of GSP for ALK at varying concentrations. 0.5 µM GSP was used for similarly conducted spike-in experiment and the Iscript reverse transcription kit was compared to SuperScript IV (ThermoFisher) (Table 2B). As measured by ddPCR the highest copy RNA signals were observed with the use of 0.5 µM GSP and the SSIV kit for reverse transcription (Table 2B).

Figure 13A:
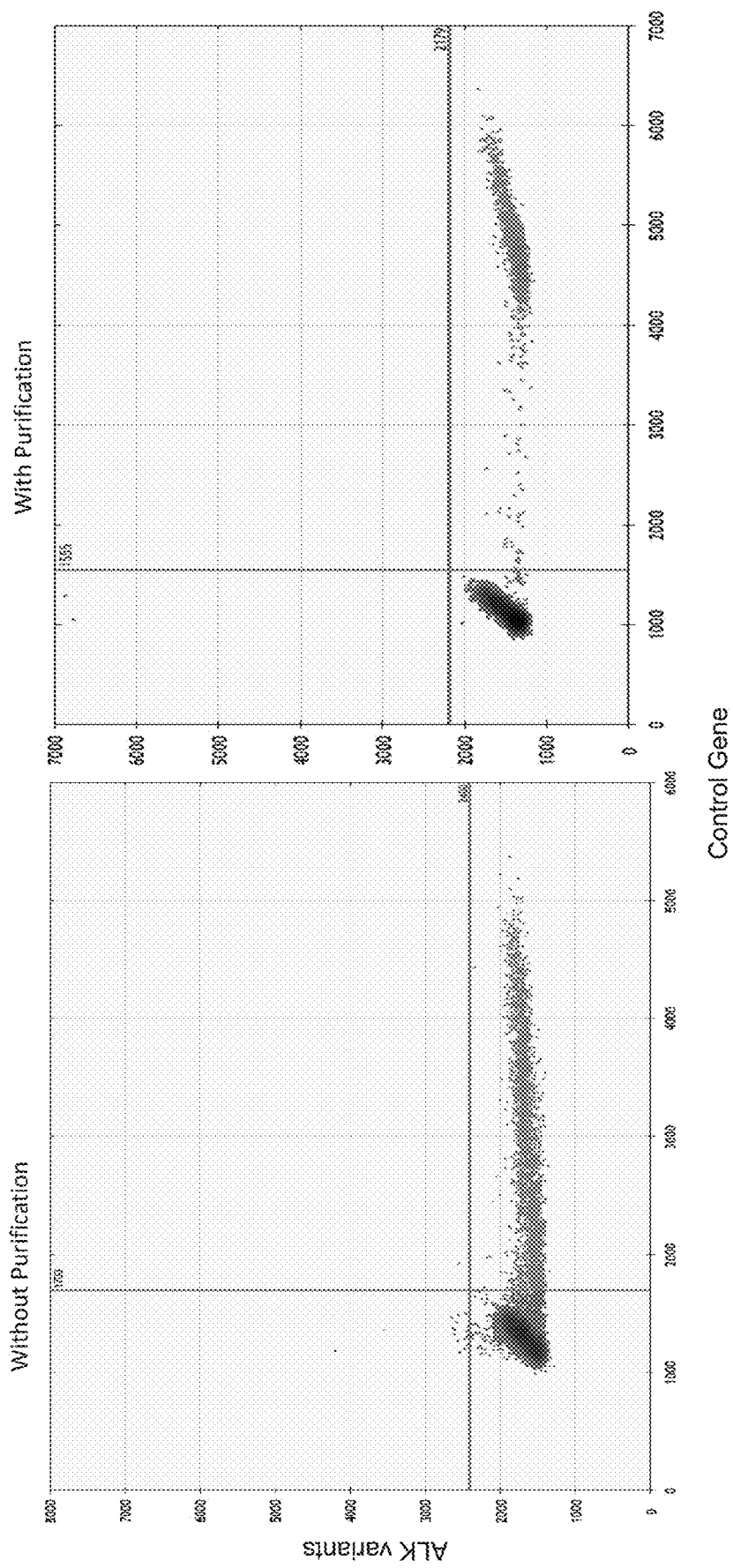
FIGS. 13A-B. cDNA Purification Improves Specificity and Efficiency of amplification. EML4-ALK RNA fragments isolated from donor samples using the GeneStrat test system were used to evaluate the impact of cDNA purification on ALK variant detection.
Figure 13B:
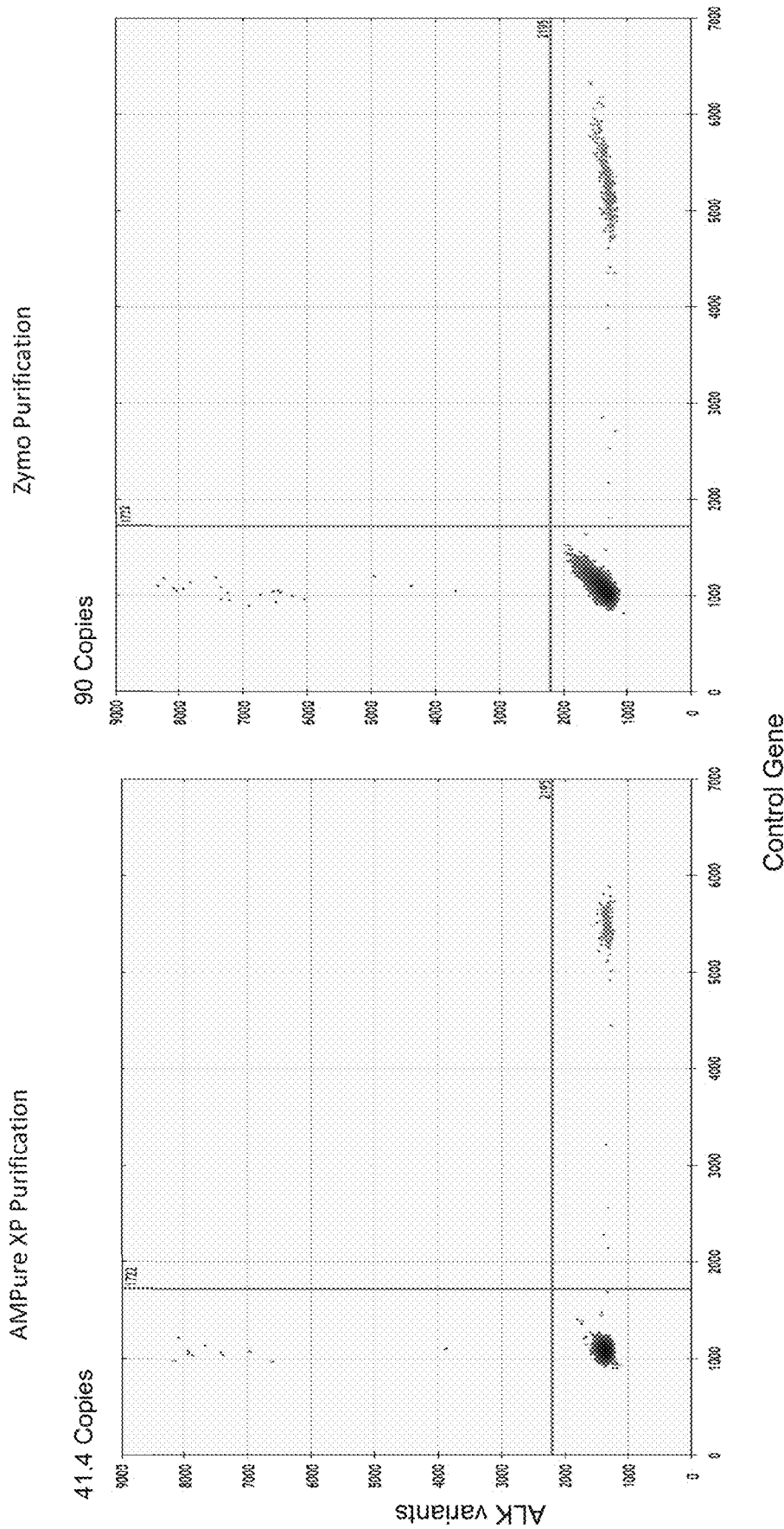

Finally, the inventors optimized their methods for RNA isolation and detection from blood by inclusion of a cDNA purification step. This step was included to reduce non-specific background and PCR inhibitors and to enhance specificity of cDNA amplification by ddPCR (FIGS. 13 A-B). In these experiments, RNA was extracted from donor samples using the Norgen Plasma/Serum Circulating and Exosomal RNA Isolation Midi Kit and concentrated using the Norgen RNA Clean-Up and Concentration Micro Kit. Two-step RT-ddPCR was performed. After cDNA generation the cDNA was divided, and half of the reaction was purified using Agencourt AMPure XP beads (Beckman Coulter). Equal amounts of purified cDNA and unpurified cDNA were used for ddPCR (FIG. 13A). AMPure XP cDNA cleanup was compared to the DNA Clean and Concentrator-5 (Zymo) method. EML4-ALK signal more than doubled with the use of the Zymo method as compared to AMPure XP (FIG. 13B). Thus, while cDNA purification generally improves the efficiency of ddPCR and results in higher signal amplitude for positive droplets, specific purification method are superior in maintaining the sensitivity of the test system.

Figure 14A:
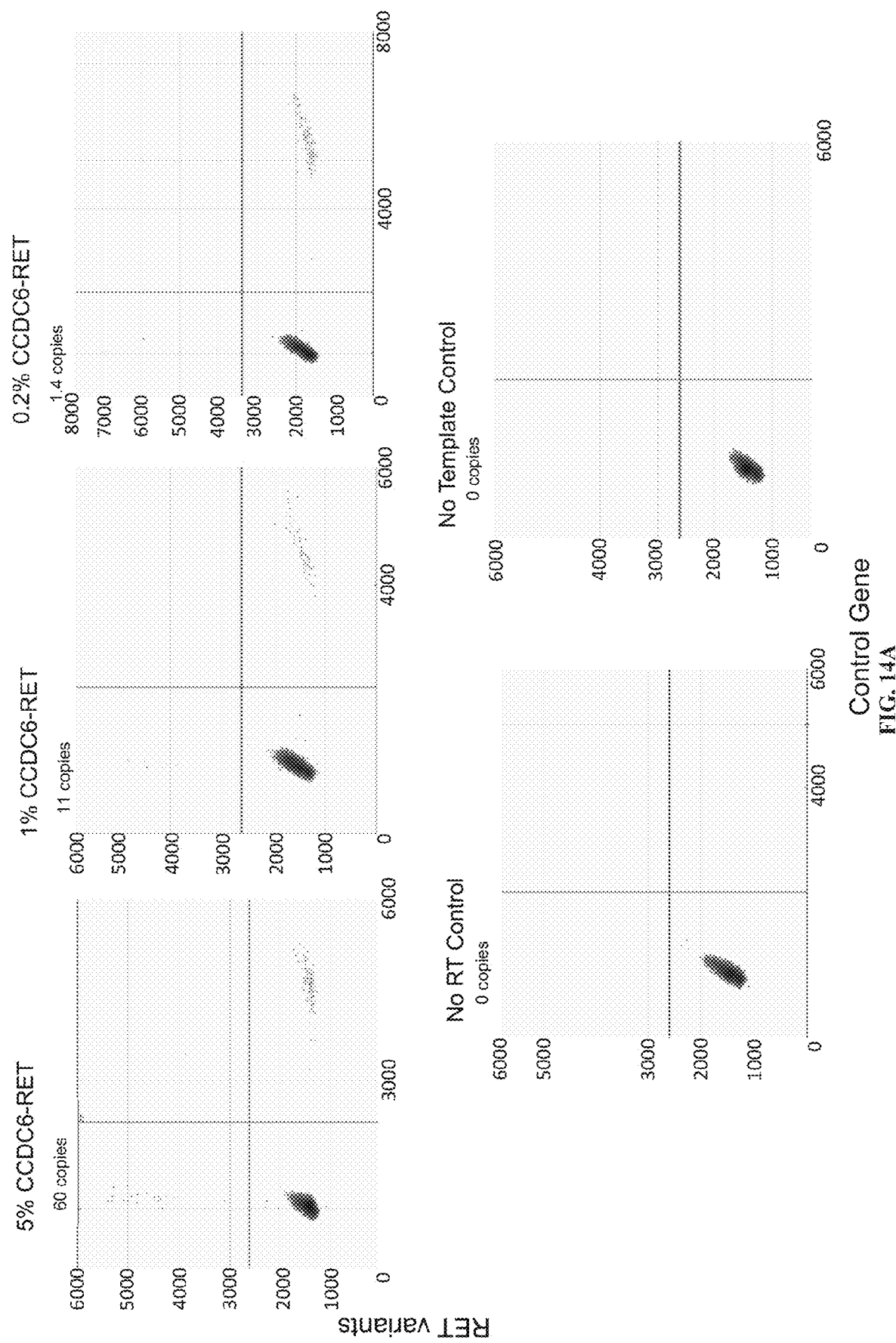
FIGS. 14A-B. Analytic Sensitivity of the GeneStrat® Gene Fusion Assays. Analytic sensitivity of (FIG. 14A) multiplex RET assay using RNA isolated from a tumor-derived cell line expressing CCDC6-RET fusion transcripts, and (FIG. 14B) multiplex ALK assay using RNA isolated from a tumor-derived cell line expressing EML4-ALK fusion transcripts. The number of copies of fusion transcript detected in each condition are shown above each 2D plot. Isolated RNA was spiked into a background of fusion transcript negative normal brain RNA at 5%, 1%, and 0.2%.
Figure 14B:
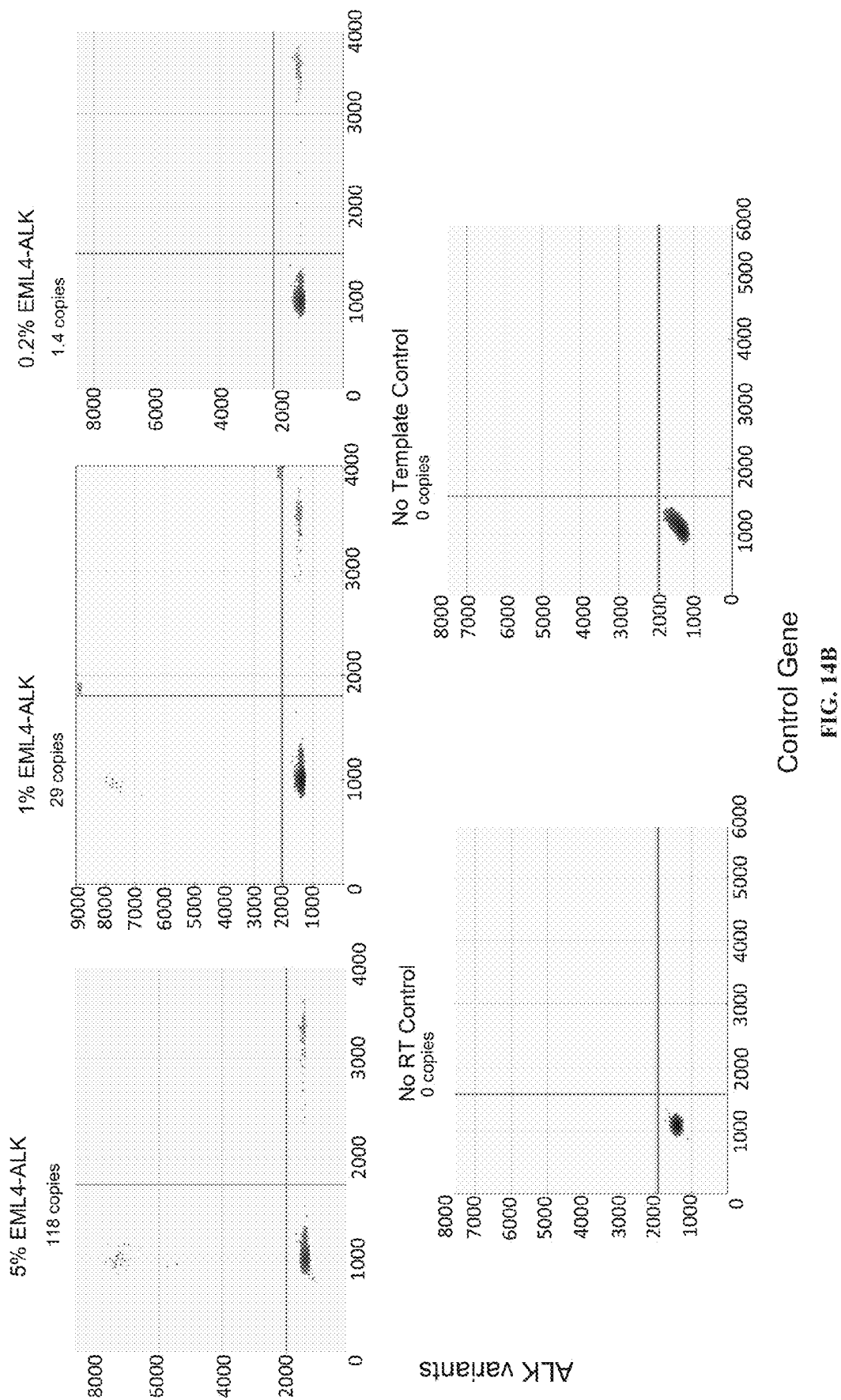

To determine the sensitivity of the final test system, circulating RNA is reverse transcribed using the SuperScript™ IV reverse transcription (RT) kit (Thermo Fisher). cDNA is isolated from remaining RT primers and reaction mix by running through the DNA Clean and Concentrator™-5 column. cDNA eluted from this column is then used for ddPCR. Examples of the lower limit of detection of this optimized test system are shown for EML4-ALK and CCDC6-RET (FIGS. 14A-B) with the sensitive detection of ROS and ALK multiplexed variant detection (lower limit of detection) of 0.2%. A no RT control and No Template Control is run with every batch to ensure specificity of the test.

mRNA Differential Expression.

In addition to the detection of cancer-specific gene targets, there is also utility in the measurement of differentially expressed molecules that may be markers of therapeutic effect, or themselves targets of therapy. In this invention, the inventors focused on the utility of blood-based testing for the measurement of genomic makers known to be regulated in malignancy. Specifically, they addressed the robust measurement of circulating mRNA in PEPs for detection using ddPCR. Evaluation criteria included droplet counts for biomarkers of cancer and immunotherapy response. Markers evaluated included, CK19, and the immune modulator PD-L1.

Programmed death-ligand 1 (PD-L1) also known as cluster of differentiation 274 (CD274) or B7 homolog 1 (B7-H1) is a protein that in humans is encoded by the CD274 gene. PD-L1 has notably been speculated to play a major role in suppressing the immune system during particular events such as pregnancy, tissue allografts, autoimmune disease and other disease states such as hepatitis. Of relevance to this invention is the finding that upregulation of PD-L1 may allow cancers to evade the host immune system. An analysis of 196 tumor specimens from patients with renal cell carcinoma found that high tumor expression of PD-L1 was associated with increased tumor aggressiveness and a 4.5-fold increased risk of death (Thompson et al., 2004). Many PD-L1 inhibitors are in development or have been commercialized as immuno-oncology therapies and are showing good results in clinical trials (Velcheti et al., 2014). Anti-PD-L1 antibodies as therapeutics include those from for example, the FDA-approved Atezolizumab/Tecentriq, (Roche Genentech) and under development, Durvalumab/MEDI4736 (Medimmune/AstraZeneca). Tests for PD-L1 detection by immunohistochemistry in tissue are FDA approved from Dako/Agilent and include the PD-L1 22C3 IHC pharmDx test as a companion diagnostic as an aid in identifying NSCLC patients for treatment with KEYTRUDA. Additionally, PD-L1 expression as detected by the PD-L1 IHC 28-8 pharmDx in non-squamous NSCLC may be associated with enhanced survival from OPDIVO® (nivolumab) treatment. Positive PD-L1 status as determined by PD-L1 IHC 28-8 pharmDx in melanoma is correlated with the magnitude of the treatment effect on progression-free survival from OPDIVO®.

In this disclosure, test development specimens included cell lines and PEP samples from normal, healthy donors and donors with NSCLC. Cell lines expressing variable levels of cytokeratins and PD-L1 were used to establish assay sensitivity. In these experiments, the test system could detect these markers in the equivalent of a single cell. The inventors evaluated specificity using RNA from these same cell lines, resting and activated lymphocytes, and monocytes using qPCR and RTR-ddPCR (FIGS. 15A-C). Specifically, RNA was extracted using the RNEasy Mini Kit (Qiagen), and cDNA was synthesized from 5 ng RNA per sample using the Superscript IV First-Strand Synthesis System (ThermoFisher). ddPCR results are shown as absolute copy number, and qPCR data is shown as expression relative to the highest-expressing sample, NCI-H441. Both methods showed a high level of concordance for the detection of PD-L1 (FIG. 15C) and detected the specific mRNA as expected.

In a second series of experiments, the inventors evaluated the utility of PEP from freshly procured whole-blood samples to assess mRNA transcript expression in EGFR mutation and wild-type specimens from donors with NSCLC (n=20) (FIGS. 16A-F). RNA was extracted and cDNA generated and purified as in the Final Assay for Recovery and Detection of Circulating RNA from plasma. ddPCR was performed using the Bio-Rad QX200 system and PrimePCR assays for CD274 (PD-L) and KRT19 (CK-19), and copy numbers as well as relative PD-L1 expression (as compared to CK-19) are shown. These test methods show that RT-ddPCR can feasibly be used to assess gene expression in PEP isolated from whole blood. Additionally, given the complexity of assessing PD-L1 in circulation because of its expression on immune cells, a threshold of 30 copies of PD-L1 was established using nine normal healthy donor specimens (FIG. 15B) (n=9). By these criteria, PD-L1 expression of sufficient copy number was restricted to a single EGFR wild-type donor (FIG. 16A; Sample 10). Previous reports have indicated that for EGFR wild-type patients, PD-L1 overexpression may be considered a poor prognostic indicator of overall survival. The inventors show here that elevated levels of mRNA from the keratins in circulation, example CK19, is also prognostic of poor patient outcomes in cancer.

Diagnostic Test System Performance: Evaluation of Assay Precision cfDNA and RNA Variants.

Technical concordance of the assays developed in this invention was assessed against reported reference results from ddPCR methods performed in an external laboratory (Horizon Discovery). The data was generated using genomic DNA from the pre-defined cell-line reference standards described above for EGFR and KRAS. The % MVF detected in each laboratory (FIG. 17A), (r=0.8117; p=0.061). Inter-operator studies were also performed for all variants. Two individual operators generated results with a high level of concordance (r=0.9333, p=0.0007).

Inter-day and intra-day precision testing was performed on three samples for each of the variants. Where available these studies were executed using cancer donor plasma samples pre-defined to have the desired mutation at variable frequencies. For EML4-ALK assays, the inventors were unable to identify donor samples of sufficient quantity for use in the precision studies. Thus EML4-ALK analytic performance data was generated using the EML4-ALK multiplexed analytic in vitro RNA standards at a high, medium and low input concentration. Intra-day testing was completed with three runs of each sample performed in a single day (FIGS. 17B-C). Inter-day was completed with one run of each sample on three consecutive days (FIGS. 17D-E). Using predefined performance criteria based on the detection of copies in all replicates and in all samples, all samples passed evaluation.

Robustness evaluation was conducted for each variant assay by analyzing the performance of the assays over 21 consecutive business days (FIGS. 18A-C). EGFR and KRAS robustness studies were executed using the multiplexed cell-line standard (custom blended by Horizon Discovery), while testing for the EML4-ALK multiplex assay was performed using multiplexed in vitro RNA standards. These controls were spiked into normal human donor plasma each day, extracted and processed through the entirety of the workflow. Consistent with criteria used in the inventors' evaluation of precision, all samples passed the robustness evaluation.

Overall, these results demonstrate the feasibility of this invention for the optimization of this test system for the prospective collection, recovery, detection and reporting of nucleic acid results (FIGS. 19A-B) from whole blood from human donors.

TABLE 1

Examples of Gene, Variant and Control Assays Shown to have Utility with the GeneStrat ® Test System

| Gene | Fusion | Variant Assay | Control assay |
| --- | --- | --- | --- |
| EGFR del19 | N/A | exon 19 deletion (ΔE746 - A750) | EGFR wt for del19 (E746 - A750) |
| EGFR del19 multiplex | N/A | p.E746_T751 > I; p.E746_A750delELREA; p.E746_A750delELREA; p.L747_T751 > Q; p.E746_S752 > D; p.L747_T751 > Q; p.L747_T751 > P; p.L747_P753 > Q; p.L747_T751 > Q; p.L747_S752delLREATS; p.L747_A750 > P; p.L747_T751delLREAT; p.L747_E749delLRE; p.L747_T751delLREAT; p.L747_P753 > S | EGFR wt |
| KRAS | N/A | KRAS G12C | KRAS wt for G12C |
| KRAS | N/A | KRAS G12D | KRAS wt for G12D |
| KRAS | N/A | KRAS G12V | KRAS wt for G12V |
| KRAS Multiplex | N/A | G12A; G12C; G12D; G12R; G12S; G12V; G13D | KRAS wt |
| BRAF | N/A | V600E | BRAF wt for V600E |
| EGFR | N/A | L858R | EGFR wt for L858R |
| EGFR | N/A | T790M | EGFR wt for T790M |
| PD-L1 | N/A | PD-L1 | CK19 |
| EML4 | ALK | E13:A20; E20:A20; E6a:A20 and E6b:A20 | GUSB |
| ROS1 | CD74 | C6:R34 | |
| | | C6:R32 | |
| | SDC4 | S2:R32 | |
| | | S2:R34 | |
| | SLC34A2 | S13del2046:R32 | |
| | | S13del2046:R34 | |
| | EZR | E10:R34 | |
| | TPM3 | T8:R35 | |
| RET | KIF5B | K15; R12 | |
| | | K16; R12 | |
| | | K22; R12 | |
| | | K23; R12 | |
| | | K24; R11 | |
| | | K24; R8 | |
| | CCDC6 | C1; R12 | |
| | TRIM33 | T14; R12 | |

Tables 2A-B. Optimization of Gene Specific
Priming and Reverse Transcriptase for Use in
cDNA Synthesis for Detection of Fusion Variants

A

| Kit | ALK Primer Final Concentration | RNA | EML4-ALK Copies |
|---|---|---|---|
| Iscript | 1 uM | denatured | 14 |
| Iscript | 0.5 uM | denatured | 24 |
| Iscript | 0.1 uM | denatured | 9.4 |
| Sensiscript | 1 uM | denatured | 18.4 |
| Sensiscript | 0.5 uM | denatured | 13.8 |
| Sensiscript | 0.1 uM | denatured | 11.6 |

B

| Spike-In | IScript | SSIV | Yield Increase with SSIV |
|---|---|---|---|
| High | 2106 | 3600 | 71 |
| Medium | 440 | 746 | 70 |
| Low | 214 | 460 | 115 |

Table 2A. Gene Specific Primers (GSPs) for EML4-ALK were designed and tested to identify the optimal concentration for use in the cDNA synthesis step of the GeneStrat® Test System. Table 2A and 2B. Comparison of various reverse transcriptase kits to optimize cDNA synthesis efficiency.

Example 2

Reverse Transcription (RT) of RNA to cDNA.

Cell Line RNA or Circulating RNA was converted to complementary DNA (cDNA) using the SuperScript IV First-Strand Synthesis System (Thermo Fisher Scientific). See Table 3 for reaction setup. RNA, primers, and deoxynucleotide triphosphates (dNTPs) were combined and incubated at 65° C. for 5 minutes, and then the mixture was cooled on ice for one minute. The remaining reaction components were then added, and the mixture was incubated according to Table 4. For the genomic DNA (gDNA) Control sample, DEPC-treated water was used instead of Reverse Transcriptase. cDNA was then either diluted by at least tenfold or purified to remove enzymes, primers, and free dNTPs using the DNA Clean and Concentrator-5 Kit according to manufacturer's instructions (Zymo Research). A 7:1 binding buffer-to-sample ratio was used for binding of the DNA to the Zymo column. cDNA was used immediately in ddPCR reactions or stored at −80° C.

TABLE 3

Reverse Transcription Reaction Components

| Volume (μL) | Component |
|---|---|
| 1/primer | 50 ng/μl random hexamer primers and/or 50 μM Oligo dT primer and/or gene-specific primer |
| 1 | 10 mM (each) dNTP mix |
| 9 | RNA |
| 4 | 5x SuperScript Buffer |

TABLE 3-continued

Reverse Transcription Reaction Components

| Volume (μL) | Component |
|---|---|
| 1 | 100 mM Dithiothreitol |
| 1 | RNase-Out Ribonuclease Inhibitor (40 U/μl) |
| 1 | SuperScript IV Reverse Transcriptase |
| to 20 | Nuclease-Free water |

TABLE 4

Reverse Transcription Protocol

| Temperature | Time |
|---|---|
| 23° C. | 10 minutes |
| 50° C. | 10 minutes |
| 80° C. | 10 minutes |
| 4° C. | Hold |

Digital Droplet PCR (ddPCR).

Reaction mixtures were prepared for multiplexed detection of PD-L1 and CK19 RNA according to Table 5. ddPCR emulsions were generated using 20 μL of reaction mixture and 70 μL of droplet generation oil using the QX200 Droplet Generator (Bio-Rad). Following droplet generation, the ddPCR emulsion was transferred to a fresh PCR plate, and amplification/signal generation was performed according to the thermal-cycling protocol listed in Table 6.

A novel assay was designed for detection of Cytokertatin 19 (CK19, also referred to as Keratin 19; encoded by the KRT19 gene) mRNA. This intron-spanning assay contains a forward primer complementary to sequence within Exon 1 of the CK19 gene, a reverse primer complementary to sequence within Exons 1 and 2 of the CK19 gene, and a probe which is complementary to sequence within Exon 1 and conjugated to a HEX fluorophore as well as a quencher. The assay was optimized to be run either individually or in a multiplexed format. The CK19 Assay primers and probe sequences are listed in Table 7.

TABLE 5 ddPCR Reaction Components

| Volume (μL) | Component |
|---|---|
| 10 | ddPCR Supermix for Probes, No dUTP (Bio-Rad) |
| 1 | 20x PD-L1 Assay (Bio-Rad) |
| 1 | 20x CK19 Assay (900 nM primers, 250 nM 5'-hexachlorofluorescein-CE phosphoramidite probe) |
| 8 | cDNA diluted in nuclease-free water |
| 20 | Total Volume |

TABLE 6 ddPCR Protocol

| Cycling Step | Temperature, ° C. | Time | Ramp Rate | # Cycles |
|---|---|---|---|---|
| Enzyme activation | 95 | 10 min | ~2° C./sec | 1 |
| Denaturation | 94 | 30 sec | | 40 |
| Annealing/extension | 55 | 1 min | | |

TABLE 6-continued ddPCR Protocol

| Cycling Step | Temperature, °C. | Time | Ramp Rate | # Cycles |
|---|---|---|---|---|
| Enzyme deactivation | 98 | 10 min | | 1 |
| Hold (optional) | 4 | infinite | ~1° C./sec | 1 |

*Use a heated lid set to 105° C. and set the sample volume to 40 μl.

TABLE 7

Components of the ddPCR Assay for CK19

| Component | Sequence |
|---|---|
| Forward Primer | GCGACTACAGCCACTACTAC (SEQ ID NO: 2) |
| Reverse Primer | GTGGCACCAAGAATTTGTCC (SEQ ID NO: 3) |
| Probe | ACGACCATCCAGGACCTGCG (SEQ ID NO: 1) |

Plate Reading and Data Analysis.

Plates were then read using the QX200 Droplet Reader (Bio-Rad), and results were generated and analyzed within QuantaSoft Software (Bio-Rad, Version 1.7.4.0917).

CK19 Assay Detection is Specific to RNA.

cDNA was generated from 5 ng NCI-H226 Cell Line (ATCC) RNA using random hexamers and oligo dT primers. A control reaction was also setup in parallel without reverse transcriptase enzyme to verify that the ddPCR assays do not detect genomic DNA (gDNA). cDNA was then diluted 100-fold in nuclease-free water, and 7 ul was used in a single ddPCR well for detection of PD-L and CK19. Results are shown in FIGS. 20A-C. PD-L and CK19 are detected when reverse transcriptase was used in the cDNA reaction (FIG. 1A) and not detected in the gDNA Control (FIG. 20B), indicating that both assays are specific to RNA. The ddPCR Control (ddPCR reaction assembled without cDNA) is also shown (FIG. 20C) to demonstrate that positive signal is not due to a contaminating substance in the ddPCR reaction.

CK19 Utility in Human Blood Specimens and Prognostic Value in NSCLC.

An analysis was conducted to test the association between biomarkers, especially PD-L1 and CK19 by dPCR and the NSCLC patient survival status. The inventors report on ddPCR results from summed copies from replicate reactions as described above for PD-L1 and CK19 versus PD-L1 tissue IHC scores and patient survival status. RNA was assessed prospectively in freshly collected whole-blood specimens and processed as described. The analyses were conducted for eleven patients for whom all data were available (Table 8).

TABLE 8

Human subjects with follow-up survival information available.*

| Subj | PDL1.sum | PDL1.rep1 | PDL1.rep2 | CK19.sum | CK19.rep1 | CK19.rep2 | PD-L1 Tissue IHC Score (percent TPS) | Survival status |
|---|---|---|---|---|---|---|---|---|
| I27 | 88 | 50 | 38 | 2 | 2 | 0 | 5% | alive |
| I40 | 1.8 | 0 | 1.8 | 3.4 | 0 | 3.4 | 80% | alive |
| I41 | 21.6 | 12.2 | 9.4 | 5.6 | 1.8 | 3.8 | 70% | alive |
| I42 | 82 | 42 | 40 | 2.8 | 2.8 | 0 | 90% | alive |
| I43 | 82 | 52 | 30 | 1.6 | 1.6 | 0 | 75% | alive |
| I47 | 31 | 9 | 22 | 1.8 | 1.8 | 0 | 40% | alive |
| I48 | 54 | 26 | 28 | 3.2 | 1.6 | 1.6 | 0% | alive |
| I51 | 124 | 66 | 58 | 1.6 | 1.6 | 0 | 20% | alive |
| I17 | 1014 | 542 | 472 | 7.2 | 4.2 | 3 | 0% | deceased |
| I26 | 112 | 56 | 56 | 42 | 20 | 22 | 0% | deceased |
| I28 | 44 | 22 | 22 | 21.2 | 12 | 9.2 | 95% | deceased |

*Replicate and sum of ddPCR reactions for PD-L1 and CK19 are shown along with the tumor proportion score (TPS) for tissue IHC for PD-L1. Patient survival status is also recorded.

Graphic data are shown in FIGS. 21-22. FIG. 21 shows that three deceased patients had the highest levels of circulating CK19, indicating a poor prognostic role associated with elevated levels of circulating CK19 mRNA in cancer progression and patient survival. FIG. 22 shows that, aside from the poor prognostic value associated with elevated levels of CK19 (all of the 3 larger dots are on the right side of the vertical line), the inventors did not observe any further potential associations with the PD-L1 biomarker at this time.

Kaplan-Meier curve analysis may yield additional insights to this study as the number of patients is increased and when actual survival meta data (including age, tumor stage, length of follow up, disease history, etc., and not only the survival status) become available.

Other Keratins Assessed by this Method.

Two additional keratins were tested using this RT-ddPCR system. CK8 and CK18 were detected in NCI-H226 cell line RNA. Results are shown in FIG. 2 with CK19 test results in the same cDNA sample for comparison.

Alternative Detection Methods.

Other detection methods may be paired with the novel CK19 Assay and are listed in Table 9.

TABLE 9

Alternative CK19 Detection Methods

Digital PCR
Quantitative PCR
Real-Time PCR
Crystal PCR
RainDrop PCR

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. References

The following references, to the extent that they provide exemplary procedural or other details supplementary to those set forth herein, are specifically incorporated herein by reference.

Hindson et al., High-throughput droplet digital PCR system for absolute quantitation of DNA copy number. Anal Chem 2011, 83:8604-10.

Sacher et al., Prospective Validation of Rapid Plasma Genotyping for the Detection of EGFR and KRAS Mutations in Advanced Lung Cancer. JAMA Oncol 2016.

Oxnard et al., Noninvasive detection of response and resistance in EGFR-mutant lung cancer using quantitative next-generation genotyping of cell-free plasma DNA. Clin Cancer Res 2014, 20:1698-705.

Beaver et al., Detection of cancer DNA in plasma of patients with early-stage breast cancer. Clin Cancer Res 2014, 20:2643-50.

Takeshita et al., Prognostic role of PIK3CA mutations of cell-free DNA in early-stage triple negative breast cancer. Cancer Sci 2015, 106:1582-9.

Mellert et al., Development and Clinical Utility of a Blood-based Test Service for the Rapid Identification of Actionable Mutations in NSCLC Journal of Molecular Diagnostics 2017, [In Press].

Weber et al., Detection of EGFR mutations in plasma and biopsies from non-small cell lung cancer patients by allele-specific PCR assays. BMC Cancer 2014, 14:294.

Lynch et al., Activating mutations in the epidermal growth factor receptor underlying responsiveness of non-small-cell lung cancer to gefitinib. N Engl J Med 2004, 350: 2129-39.

Paez et al., EGFR mutations in lung cancer: correlation with clinical response to gefitinib therapy. Science 2004, 304: 1497-500.

Pao et al., EGF receptor gene mutations are common in lung cancers from "never smokers" and are associated with sensitivity of tumors to gefitinib and erlotinib. Proc Natl Acad Sci USA 2004, 101:13306-11.

Yu et al., Analysis of tumor specimens at the time of acquired resistance to EGFR-TKI therapy in 155 patients with EGFR-mutant lung cancers. Clin Cancer Res 2013, 19:2240-7.

Sahnane et al., EGFR and KRAS Mutations in ALK-Positive Lung Adenocarcinomas: Biological and Clinical Effect. Clin Lung Cancer 2016, 17:56-61.

Paxton, A., Is Molecular AP testing in sync with guidelines? CAP Today, 2014.

Salgia, R., Diagnostic challenges in non-small-cell lung cancer: an integrated medicine approach. Future Oncol 2015, 11:489-500.

Yu et al., Mutation-specific antibodies for the detection of EGFR mutations in non-small-cell lung cancer. Clin Cancer Res 2009, 15:3023-8.

Janne et al., AZD9291 in EGFR inhibitor-resistant non-small-cell lung cancer. N Engl J Med 2015, 372:1689-99.

Watanabe et al., Ultra-Sensitive Detection of the Pretreatment EGFR T790M Mutation in Non-Small Cell Lung Cancer Patients with an EGFR-Activating Mutation Using Droplet Digital PCR. Clin Cancer Res 2015, 21:3552-60.

Sithanandam et al., Complete coding sequence of a human B-raf cDNA and detection of B-raf protein kinase with isozyme specific antibodies. Oncogene 1990, 5:1775-80.

Sithanandam et al., B-raf and a B-raf pseudogene are located on 7q in man. Oncogene 1992, 7:795-9.

Davies et al., Mutations of the BRAF gene in human cancer. Nature 2002, 417:949-54.

Thompson et al., Costimulatory B7-H1 in renal cell carcinoma patients: Indicator of tumor aggressiveness and potential therapeutic target. Proc Natl Acad Sci USA 2004, 101:17174-9.

Velcheti et al., Programmed death ligand-1 expression in non-small cell lung cancer. Lab Invest 2014, 94:107-16.

What is claimed:

1. A method of detecting a fragmented RNA in a freshly-collected whole blood sample from a mammalian subject comprising:
   a) recovering blood components from a whole blood sample from a mammalian subject, said blood components including plasma and buffy coat from the whole blood sample;
   b) isolating free RNA, RNA associated with, exosomes and/or platelets in platelet enriched plasma (PEP), RNA associated with PBMCs, or a combination thereof from said blood components;
   c) purifying and concentrating the isolated RNA of step (b);
   d) amplifying said RNA of step (c) or a complimentary DNA generated from said RNA of step (c) wherein generating complimentary DNA comprises performing reverse transcription of said isolated RNA using Super-Script IV reverse transcriptase;
   e) purifying and concentrating the amplified RNA; and
   f) identifying and/or quantifying amplified said RNA or complimentary DNA from step (e).

2. The method of claim 1, wherein the RNA is of sizes ranging between 50 and 250 nucleotides.

3. The method of claim 1, wherein step (b) comprises isolating said RNA from a whole blood sample that has been collected from mammalian donors into formaldehyde or formaldehyde-free preservatives and/or inhibitors of enzymes known to degrade RNA.

4. The method of claim 1, wherein steps (a)-(f) are performed in less than three days.

5. The method of claim 1, wherein the mammalian subject is a human.

6. The method of claim 1, wherein step (b) comprises isolating free RNA and/or RNA associated with exosomes and/or platelets in said PEP.

7. The method of claim 1, further comprising generating an integrated test result report (iTRR) integrating physician information, patient information, reimbursement information, and/or treatment recommendation or impact, with the results from step (e), such as a serum protein test result.

8. The method of claim 1, further comprising one or more control reactions.

9. The method of claim 1, further comprising quantifying said RNA or complimentary DNA from step (d) using dPCR, qPCR, or NGS.

10. The method of claim 1, wherein 2 or more copies of variant target are detected by dPCR and are validated against mammalian donor samples as the cut-off for a positive DNA or RNA-fusion mutation.

11. The method of claim 1, wherein elevated levels of differentially-expressed target are detected by dPCR when validated compared to normal healthy mammalian donor samples as the cut-off for a positive result.

12. The method of claim 1, where the RNA is obtained from components of the buffy-coat fraction of processed whole-blood from cancer patients, including but not limited to malignant tumor cells, lymphocytes, granulocytes, neutrophils, dendritic cells.

13. The method of claim 1, further comprising obtaining said whole blood sample from the subject.

14. The method of claim 13, wherein said whole blood sample is obtained using a specimen collection kit configured for collection and ambient temperature shipment of fractionated or whole blood, wherein the collection kit is configured to allow downstream molecular proteomic and/or genomic analysis of the blood components.

15. A method of detecting a cytokeratin nucleic acid in a sample comprising:
   a) obtaining a cytokeratin RNA containing sample;
   b) annealing forward and reverse primers that hybridize to said cytokeratin nucleic acid with said sample;
   c) amplifying said cytokeratin RNA; and
   d) detecting amplified cytokeratin RNA.

* * * * *